US012079959B2

(12) United States Patent
Iwasa

(10) Patent No.: US 12,079,959 B2
(45) Date of Patent: Sep. 3, 2024

(54) IMAGE PROCESSING DEVICE

(71) Applicant: NIKON CORPORATION, Tokyo (JP)

(72) Inventor: Akio Iwasa, Yokohama (JP)

(73) Assignee: NIKON CORPORATION, Tokyo (JP)

(*) Notice: Subject to any disclaimer, the term of this patent is extended or adjusted under 35 U.S.C. 154(b) by 293 days.

(21) Appl. No.: 17/690,591

(22) Filed: Mar. 9, 2022

(65) Prior Publication Data
US 2022/0270226 A1 Aug. 25, 2022

Related U.S. Application Data

(63) Continuation of application No. PCT/JP2020/032732, filed on Aug. 28, 2020.

(30) Foreign Application Priority Data

Sep. 17, 2019 (JP) .................. 2019-168631

(51) Int. Cl.
G06T 5/50 (2006.01)
G06T 3/60 (2006.01)
(Continued)

(52) U.S. Cl.
CPC ............... G06T 5/50 (2013.01); G06T 3/60 (2013.01); G06T 5/70 (2024.01); G06T 7/11 (2017.01);
(Continued)

(58) Field of Classification Search
USPC ....... 358/1.1–3.29, 1.11–1.18; 382/100–308; 345/581–654; 600/481–544, 921;
(Continued)

(56) References Cited

U.S. PATENT DOCUMENTS

2004/0066978 A1* 4/2004 Nanbu ................. G06T 5/20
382/128
2006/0257013 A1* 11/2006 Ramm ............... G01N 33/5026
382/133
(Continued)

FOREIGN PATENT DOCUMENTS

JP 2001-283215 A 10/2001
JP 2009-226141 A 10/2009
(Continued)

OTHER PUBLICATIONS

International Written Opinion and Search Report issued in corresponding International Patent Application No. PCT/JP2020/032732 on Nov. 2, 2020.
(Continued)

Primary Examiner — Marcellus J Augustin
(74) Attorney, Agent, or Firm — Squire Patton Boggs (US) LLP

(57) ABSTRACT

An image processing device includes first image processing part, and first image processing part includes first pixel group setting part that sets plurality of first pixel groups which is set to correspond to first pixel, and which is disposed along in plurality of directions that form plurality of angles different from each other with respect to predetermined direction in first image or which is disposed along in predetermined direction in each of plurality of images obtained by moving first image by plurality of angles different from each other with respect to predetermined direction, first calculation part configured to calculate plurality of first candidate pixel values based on size of pixel value of pixel included in each of plurality of first pixel groups, and first pixel value setting part that sets pixel value of second pixel of second image based on plurality of first candidate pixel values.

14 Claims, 23 Drawing Sheets

(51) Int. Cl.
  *G06T 5/70* (2024.01)
  *G06T 7/11* (2017.01)
  *G06T 7/136* (2017.01)
(52) U.S. Cl.
  CPC .... *G06T 7/136* (2017.01); *G06T 2207/30024* (2013.01); *G06T 2207/30101* (2013.01)
(58) Field of Classification Search
  USPC ........................................ 706/1–62, 900–903
  See application file for complete search history.

(56) References Cited

U.S. PATENT DOCUMENTS

| | | | |
|---|---|---|---|
| 2009/0154792 A1 | 6/2009 | Sun et al. | |
| 2010/0142792 A1* | 6/2010 | Sakaguchi | A61B 6/03 382/128 |
| 2015/0193665 A1* | 7/2015 | Fukuda | G06T 3/14 382/115 |
| 2015/0248757 A1* | 9/2015 | Ohishi | G06T 7/11 382/131 |
| 2018/0211382 A1 | 7/2018 | Igarashi et al. | |

FOREIGN PATENT DOCUMENTS

| | | |
|---|---|---|
| JP | 2016-212092 A | 12/2016 |
| JP | 2017-6296 A | 1/2017 |
| JP | 2019-074496 A | 5/2019 |

OTHER PUBLICATIONS

Changming Sun et al., "Fast Linear Feature Detection Using Multiple Directional Non-Maximum Suppression", ResearchGate, 18th International Conference on Pattern Recognition (ICPR'06), DOI: 10.1109/ICPR.2006.548, https://www.researchgate.net/publication/220929025, 5 pages.

Communication forwarding the extended European Search Report dated Oct. 11, 2023 for European Patent Application No. 20866601.6; 12 pages.

Notification of First Office Action dated Apr. 29, 2024 for Chinese Patent Application No. 202080077783.7; with English translation, 25 pages.

* cited by examiner

IMAGE PROCESSING DEVICE

CROSS-REFERENCE TO RELATED APPLICATION

Priority is claimed on Japanese Patent Application No. 2019-168631, filed on Sep. 17, 2019, the content of which is incorporated herein by reference. The present application is a continuation application of International Application PCT/JP2020/032732, filed on Aug. 28, 2020. The contents of the above applications are incorporated herein.

BACKGROUND

Technical Field

The present invention relates to an image processing device, an image processing method and a program.

For example, a method of performing image processing with respect to an image obtained by imaging an object including a linear portion such as a branch or the like that is a morphological feature is proposed (for example, see US Unexamined Patent Application, First Publication No. 2009/0154792). When processing of reducing noise in such image processing is performed, it is necessary to perform the processing while leaving information about the linear portion.

SUMMARY

According to a first aspect of the present invention, an image processing device includes a first image processing part configured to set a pixel value of a second pixel of a second image which is located at a position corresponding to a first pixel of a first image, which is obtained through imaging, in the second image obtained through image processing of the first image, a second image processing part configured to set a pixel value of a third pixel located at a position corresponding to the first pixel in a third image obtained by image processing of the first image, and a third image processing part configured to generate a weighted image on the basis of the pixel value of the second pixel processed by the first image processing part and the pixel value of the third pixel processed by the second image processing part, wherein the first image processing part comprises: a first pixel group setting part configured to set a plurality of first pixel group which is set to correspond to the first pixel and which includes pixels disposed along in one direction; a first calculation part configured to calculate a first candidate pixel values in each of the plurality of first pixel groups on the basis of a size of the pixel value of the pixel included in each of the plurality of first pixel groups; and a first pixel value setting part configured to set the pixel value of the second pixel of the second image on the basis of the plurality of first candidate pixel values, the second image processing part comprises: a second pixel group setting part configured to set a plurality of second pixel groups which is set to correspond to the first pixel and which includes pixels disposed along in at least two directions; a second calculation part configured to calculate a second candidate pixel value of each of a plurality of second pixel groups on the basis of a size of the pixel value of the pixel included in each of a plurality of second pixel groups; and a second pixel value setting part configured to set a pixel value of a third pixel of the third image on the basis of a plurality of second candidate pixel values.

DESCRIPTION OF THE EMBODIMENTS

Hereinafter, an embodiment of the present invention will be described with reference to the accompanying drawings.

First Embodiment

Figure 1:
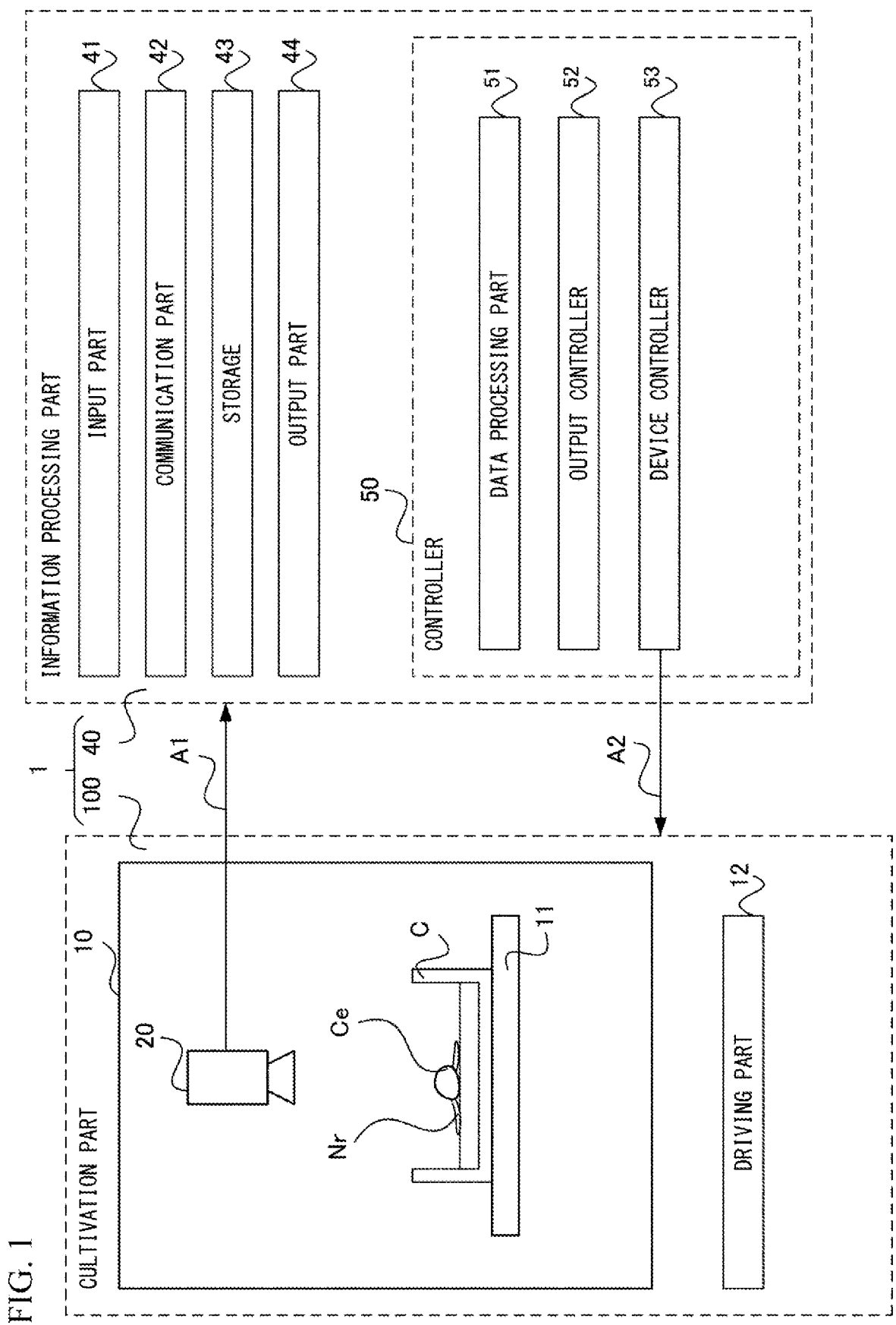
FIG. 1 is a conceptual view showing a configuration of an image processing device of a first embodiment.

FIG. 1 is a conceptual view showing a configuration of an image processing device of the embodiment. An image processing device 1 includes a cultivation part 100 and an information processing part 40. The cultivation part 100 includes a cultivation room (a cultivation chamber) 10, a specimen observation table (a stage) 11, a driving part 12, and an imaging part 20. The information processing part 40 includes an input part 41, a communication part 42, a storage 43, an output part 44, and a controller 50. The controller 50 includes a data processing part 51, an output controller 52, and a device controller 53.

The image processing device 1 is configured as a cultivation device, and has a configuration in which captured image data that are image data obtained by imaging a sample (for example, a cell) in the cultivation part 100 is input and processed by the data processing part 51.

In the embodiment, image processing of emphasizing linear portions including straight lines, curved lines, polygonal lines, crosses, or the like from the captured image corresponding to the captured image data is performed. Here, "emphasize" means making it easier to distinguish the linear portions from other portions (for example, a background portion, a non-linear portion) by pixel values, and is not limited to a case in which the luminance of the linear portion increases. Hereinafter, while an example in which a cell Ce is a neuron and a portion corresponding to a neurite Nr is emphasized as the linear portion will be described, as long as the above-mentioned linear portions are included, an object to be emphasized is not limited to this example, and may be an arbitrary element (for example, another cell or something other than cells) that constitutes an image.

Further, the above-mentioned image processing may be performed on images other than the captured image, such as a drawing image or the like.

The cultivation part 100 includes the cultivation room 10 configured to cultivate the cell Ce, and imaging of the cell Ce cultivated in the cultivation room 10 is performed by the imaging part 20.

The cultivation room 10 accommodates a cultivation container C in which the cell Ce is cultivated. The cultivation container C is, for example, a well plate or a dish. A temperature regulator (for example, a heater) and a temperature sensor (not shown) controlled by the controller 50 are disposed in the cultivation room 10. The inside of the cultivation room 10 is controlled such that cultivation of the cell Ce is performed under a preset environment, for example, being maintained at a temperature set by the temperature regulator and the temperature sensor in advance. The driving part 12 includes an actuator, moves the cultivation container C to place it on the specimen observation table 11 inside the cultivation room 10 at a previously determined time. Further, the driving part 12 moves the imaging part 20, the specimen observation table 11, or the like to an appropriate position (for example, an observation position) in an optical axis direction such that the cell Ce is disposed on a focal surface on the imaging part 20 for the purpose of imaging the cell Ce.

The imaging part 20 includes an imaging device including an imaging element such as a CMOS, a CCD, or the like, and images the cell Ce, in particular, the neurite Nr of the cell Ce. An imaging method by the imaging part 20 is not particularly limited as long as the pixel corresponding to the neurite Nr can be distinguished from other portions by a luminance value of such pixel or luminance value of a plurality of pixels around such pixel with desired accuracy in the captured image including the cell Ce. For example, as the imaging method by the imaging part 20, a fluorescence observation method, a phase difference observation method, or the like can be used. In the case of the fluorescence observation method, the imaging part 20 acquires a fluorescent image of a sample and the fluorescent image is used for the image analysis which will be described in the following, and in the case of the phase difference observation method, the imaging part 20 acquires a phase difference image of a sample and the phase difference image is used for the image analysis which will be described in the following.

When the imaging part 20 performs imaging using the fluorescence observation method, fluorescent dyeing can be performed according to a gene instruction by expressing a fluorescent protein such as a green fluorescent protein (GFP) or the like in the cell Ce, or expressing a protein localized in the neurite Nr and a protein fused with the fluorescent protein. Another labeling method such as immunostaining or the like may be performed as long as it does not cause any problems with use of the cell Ce after imaging (for example, cultivation, transfer, or pickup).

A pixel signal obtained through imaging of the cell Ce by the imaging part 20 is converted into a digital signal, input into the information processing part 40 as captured image data to which the pixel and the luminance value correspond (an arrow A1 of FIG. 1), and stored in the storage 43.

The information processing part 40 serves as an interface with the user of the image processing device 1 (hereinafter, simply referred to as "a user"), and also performs processing on various data such as communication, storage, computation, or the like.

Further, the information processing part 40 may be configured as an information processing device physically separated from the cultivation part 100. In addition, at least some of the data used by the image processing device 1 may be stored in a remote server or the like connected by a network.

The input part 41 includes input devices such as a mouse, a keyboard, various buttons, a touch panel, or the like. The input part 41 receives data or the like required for imaging by the cultivation part 100 or data processing by the data processing part 51 from the user.

The communication part 42 includes a communication device that is communicable with the Internet or the like in a wireless or wired manner, and appropriately transmits and receives data related to control or processing in the image processing device 1.

The storage 43 includes a non-volatile storage medium, and stores a program that performs processing in the controller 50, image data related to the processing of the data processing part 51, and the like.

The output part 44 includes a display device such as a liquid crystal monitor or the like, and outputs an image or the like indicating information obtained by processing of the data processing part 51.

The controller 50 is constituted by a processing device such as a CPU or the like, functions as a main constituent of an operation of controlling the image processing device 1, and performs various types of processing by executing the program installed in the storage 43.

The data processing part 51 of the controller 50 acquires and processes the captured image data input from the imaging part 20, and generates an image in which the linear portion in the captured image is emphasized. Hereinafter, the image is referred to as a weighted image.

Figure 2:
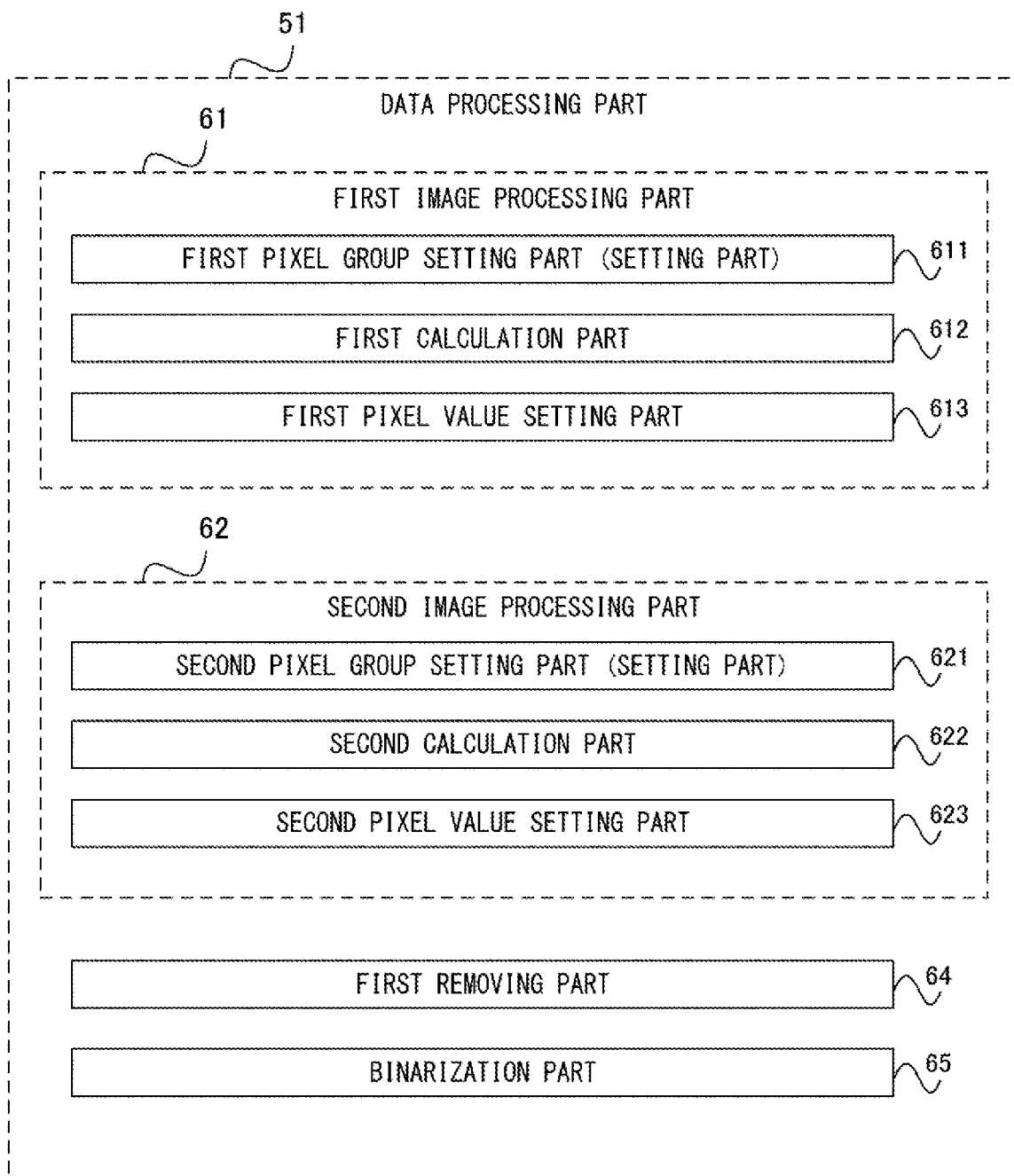
FIG. 2 is a conceptual view showing a configuration of a data processing part according to the first embodiment.

FIG. 2 is a conceptual view showing a configuration of the data processing part 51. The data processing part 51 includes a first image processing part 61, a second image processing part 62, a first removing part 64, and a binarization part 65. The first image processing part 61 includes a first pixel group setting part 611, a first calculation part 612, and a first pixel value setting part 613. The second image processing part 62 includes a second pixel group setting part 621, a second calculation part 622, and a second pixel value setting part 623. The first pixel group setting part 611 and the second pixel group setting part 621 constitute a setting part.

The first image processing part 611 of the data processing part 51 performs image processing on the captured image data corresponding to the captured image, and generates first weighted image data corresponding to the first weighted image. Hereinafter, the image processing by the first image processing part 611 is referred to as first image processing. Here, the first weighted image is a weighted image in which a linear portion (for example, the neurite Nr) in the captured image is emphasized by the first image processing. The first image processing part 611 sets a pixel value of the first weighted image corresponding to each pixel in the captured image. Hereinafter, a pixel that is an object of the processing by the first image processing part 61 in the captured image is referred to as a first pixel, and a pixel in the first weighted image corresponding to the first pixel is referred to as a second pixel. Here, while "corresponding" of the first pixel and the second pixel means that these pixels indicate the luminance of the subject by the light from the same position in the captured image, the position allows a constant deviation as long as desired analysis accuracy is obtained.

Figure 3:
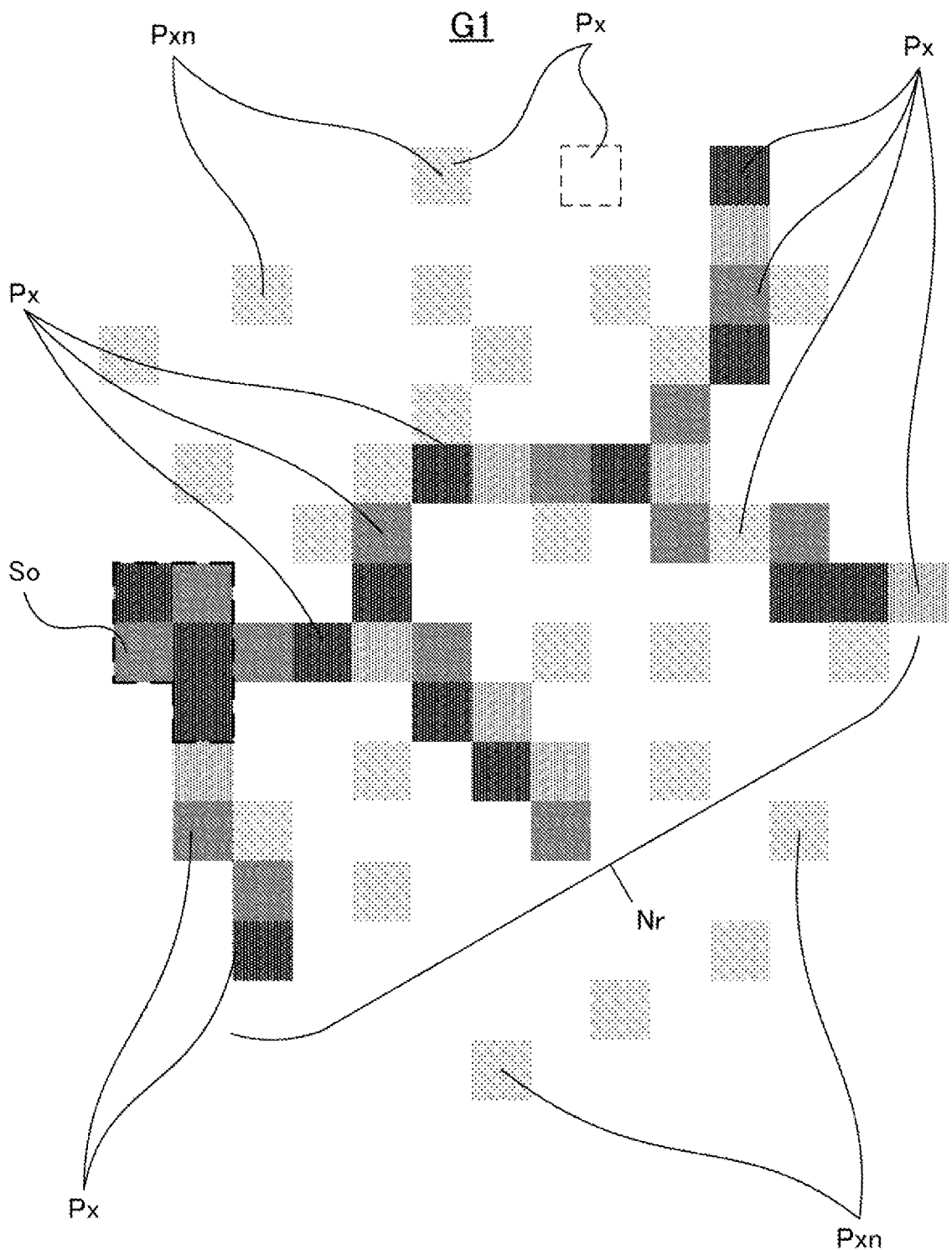
FIG. 3 is a conceptual view showing a captured image according to the first embodiment.

FIG. 3 is a conceptual view showing an example of the captured image. A captured image G1 is constituted by a plurality of pixels Px. In the example of FIG. 3, it is shown that, as hatching of a portion becomes darker, luminance of the pixel becomes higher. In the captured image G1 of FIG. 3, a cell body So and the neurite Nr are shown as portions with high luminance. Meanwhile, noise pixels Pxn that are pixels having luminance due to noise or the like in the imaging are also scattered in the captured image G1. One of the reasons is that the imaging cannot be performed with sufficient accuracy because a pixel signal corresponding to the linear portion such as the neurite Nr or the like is weak during the imaging. In particular, this tendency is also seen in a fluorescence microscope often used for imaging of a cell or the like.

Further, an expressing method of the image in the captured image data is not particularly limited, and for example, the larger the pixel value, the higher the brightness or chroma, and the smaller the pixel value, the higher the brightness or chroma.

In cultivation of the neuron, the neuron is evaluated by measuring numerical values such as a length (or a width), the number of branches, and the like of the neurite Nr. Proper extraction of neurites from the captured image is necessary for accurate neuron evaluation. In the captured image G1 having the noise pixel Pxn as shown in FIG. 3, it may be difficult to extract the linear portion accurately. The image processing device 1 of the embodiment facilitates the proper extraction of the neurite Nr by generating the image that emphasizes the linear portion in the captured image.

Further, in addition to the evaluation of the neurite, the image processing device 1 of the embodiment can be used for various purposes such as utilization, extraction, analysis, or the like of the linear portion in the image. In addition, in the cell body So, it is possible to previously detect a portion corresponding to the cell body So from the captured image, and perform the following first image processing or the like by masking the portion. Detection of the cell body So can be appropriately performed by removing details of the captured image using opening processing, closing processing, and the like.

The first pixel group setting part 611 of the first image processing part 61 sets a plurality of first pixel groups corresponding to the first pixel of the captured image G1.

Figure 4:
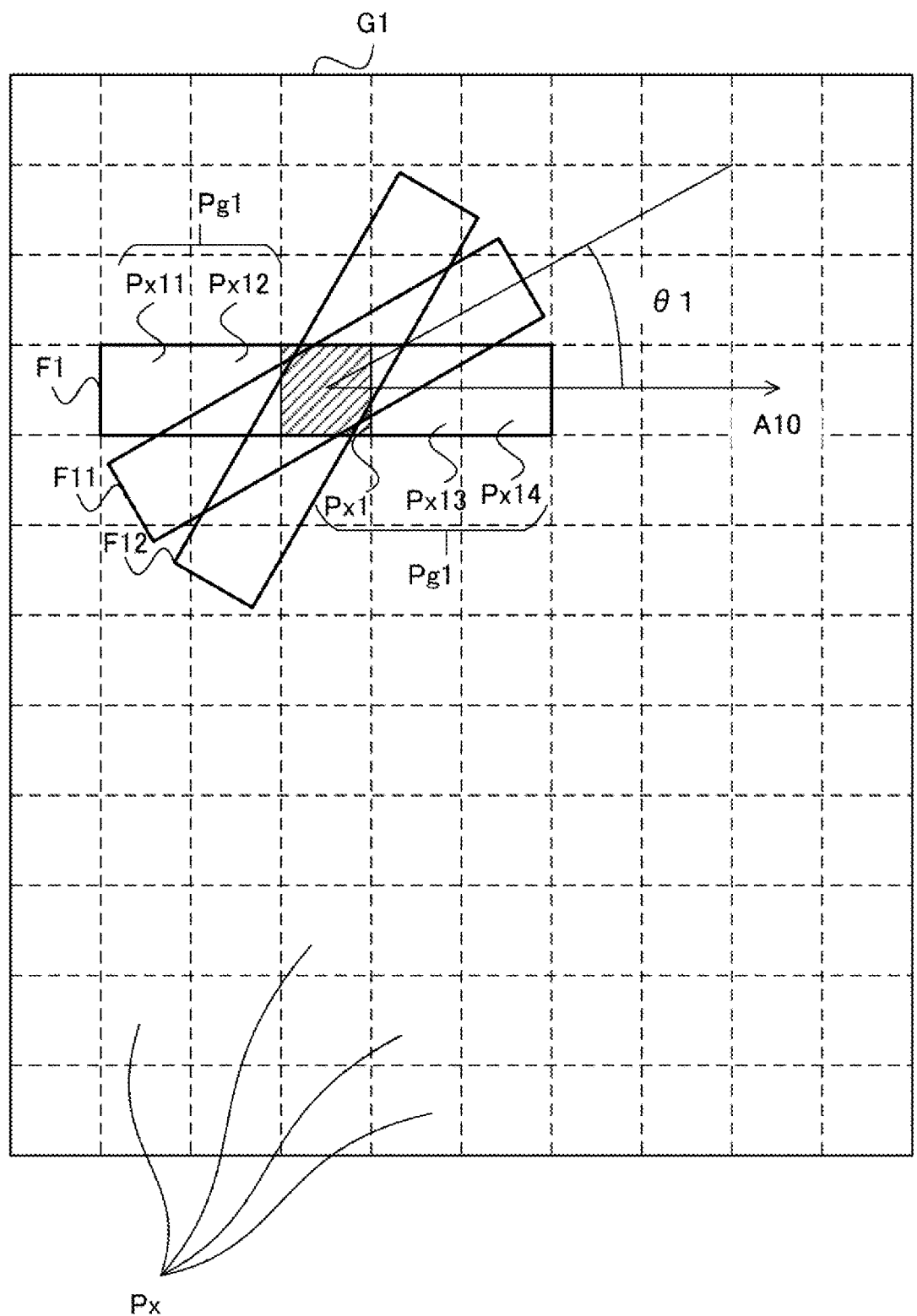
FIG. 4 is a conceptual view for describing first image processing according to the first embodiment.

FIG. 4 is a conceptual view for describing the first image processing. The first pixel group setting part 611 selects a first pixel Px1 from the pixels Px included in the captured image G1. The first pixel group setting part 611 selects and sets the first pixel Px1 from the pixels included in a region previously set by the first image processing part 61 and in which the first pixel Px1 is set in the captured image G1 (hereinafter referred to as a target region).

While the target region may be the entire captured image, for example, when the pixel located on a peripheral portion of the captured image G1 is set as the first pixel Px1, there may be no pixel corresponding to the following one-dimensional filter. Accordingly, in this case, it is preferable for virtual pixels to be appropriately supplemented around the captured image G1 and the following image processing to be performed with desired accuracy. The target region can be set in a portion excluding a peripheral portion of about a half of a length of the one-dimensional filter from the captured image G1 such that there is no pixel corresponding to the following one-dimensional filter.

The first pixel group setting part 611 includes the first pixel Px1, and sets a pixel group disposed along in a plurality of directions that form a predetermined angle with respect to a reference direction as a first pixel group Pg1. The predetermined angle is referred to as a first angle $\theta 1$ hereinbelow. The reference direction is a leftward/rightward direction of the captured image G1 in FIG. 4 (see an arrow A10), but it is not particularly limited thereto and may be any direction. In FIG. 4, the plurality of pixels Px11, Px12, Px1, Px13 and Px14 included in the first pixel group Pg1 when the first angle $\theta 1$ is 0° are shown. The first pixel group Pg1 preferably includes a plurality of pixels arranged in one direction and adjacent to each other in this way. The first pixel group setting part 611 can set a plurality of pixels arranged in an inclination direction and a longitudinal direction and adjacent to each other in the captured image G1 as the first pixel group Pg1 when the first angle $\theta 1$ is 45° and 90°.

In FIG. 4, partial regions of the captured image G1 corresponding to the first pixel group Pg1 when the first angle $\theta 1$ is 0°, 30° and 60° are schematically shown by one-dimensional filters F1, F11 and F12, respectively. When the first pixel group Pg1 corresponding to the one-dimensional filters F11 and F12 is set, pixels overlapping these one-dimensional filters or pixels through which a straight line corresponding to these one-dimensional filters passes can be included in the first pixel group Pg1. However, since the pixels set in this way are not arranged on a straight line, the accuracy decreases slightly.

Accordingly, in actual calculation, the first pixel group setting part 611 preferably sets a plurality of pixels disposed around a pixel corresponding to the first pixel in a predetermined direction as the first pixel group Pg1 in the image obtained by rotating the captured image G1 in a direction that forms the first angle $\theta 1$ with respect to a reference direction. The predetermined direction is not particularly limited, and may be an arbitrary direction such as a reference direction or the like. In the example of FIG. 4, the first pixel group setting part 611 rotates the captured image G1 clockwise by $\theta 1$ while fixing the one-dimensional filter F1, and sets pixels of vertical 1× horizontal 5 pixels within a range of the one-dimensional filter F1 in the obtained image as the first pixel group Pg1. Accordingly, the first pixel group Pg1 corresponding to the one-dimensional filter F11 in the captured image G1 before rotation can be more accurately set than in a case in which the first pixel group Pg1 is set by rotating the one-dimensional filter.

The first pixel group setting part 611 sets each of the first pixel groups Pg1 for the plurality of first angles $\theta 1$. The plurality of first angles $\theta 1$ are set for predetermined angles selected from a range of, for example, 1° to 45° or the like. For example, the first pixel group setting part 611 can set the plurality of first angles θ1 from 0° to 179° by 1°, and set the first pixel group Pg1 for each of the first angles θ1.

The number of the pixels that constitute the first pixel group Pg1 is not particularly limited as long as the number is 2 or more. The number of the pixels can be set on the basis of a curvature, a radius of curvature, or the like of the linear portion in the captured image G1.

Further, the first pixel group Pg1 may be a pixel group constituted by a plurality of rows, for example, a pixel block of 2 pixels×5 pixels or the like. In this case, the pixel number arranged in one direction preferably exceeds two times the pixel number arranged in the other direction.

The first calculation part 612 of the first image processing part 61 calculates a first candidate pixel value on the basis of the pixel value of the pixel included in the first pixel group Pg1. The first candidate pixel value is a value that is a candidate of a pixel value set to a second pixel corresponding to the first pixel Px1 in the first weighted image. In other words, the pixel value set to the second pixel is selected from a plurality of first candidate pixel values.

The first calculation part 612 calculates an average value of the pixel values of the pixels included in the first pixel group Pg1 and sets the average value as the first candidate pixel value. For example, the first calculation part 612 calculates an arithmetic mean of the pixels of the pixels Px11, Px12, Px1, Px13 and Px14 corresponding to the one-dimensional filter F1, and sets the arithmetic mean as the first candidate pixel value of the first pixel group Pg1 corresponding to the one-dimensional filter F1. The first calculation part 612 calculates a first candidate pixel value for each of the first pixel groups Pg1 set by the first pixel group setting part 611. The first calculation part 612 calculates a first candidate pixel value for the first pixel groups Pg1 corresponding to the plurality of first angles θ1.

Further, the first calculation part 612 may calculate an average value of the pixel values of the pixels included in the first pixel group Pg1 as the first candidate pixel value according to an average other than the arithmetic mean, for example, a geometrical mean or the like. Alternatively, the first calculation part 612 can set a sum of the pixel values of the pixels included in the first pixel group Pg1 or a value obtained by adjusting the sum according to a numerical range that is settable as a pixel value through appropriate adjustment of standardization or the like as a first candidate pixel value. Like the sum or the average, a calculation method of a first candidate pixel value set by the first calculation part 612 is not particularly limited as long as the first candidate pixel value can be set on the basis of the entire size of the pixel values of the pixels included in the first pixel group Pg1.

The first pixel value setting part 613 of the first image processing part 61 sets a pixel value of the second pixel in the first weighted image corresponding to the first pixel Px1 from a plurality of first candidate pixel values calculated for the first pixel Px1.

The first pixel value setting part 613 can set a pixel value of a second pixel corresponding to the largest value among the plurality of first candidate pixel values for the first pixel Px1. This means that, in the first image processing, the pixel value by the one-dimensional filter, which corresponds to a direction in which the highest pixel of the pixel values is arranged among the one-dimensional filters F, F11 and F12 in the plurality of directions, is reflected in the first weighted image. As a result, when a possibility that the pixel corresponds to the linear portion such as the neurite Nr or the like increases as the pixel value increases, the linear portion can be emphasized during smoothing. The first pixel value setting part 613 can set the smallest value of the plurality of first candidate pixel values for the first pixel Px1 as the pixel value of the corresponding second pixel. Accordingly, when the possibility that the pixel corresponds to the linear portion increases as the pixel value decreases, the linear portion can be emphasized during the smoothing.

Further, the pixel value of the second pixel may be set as the value of a range of 0.8 times to 1.2 times, preferably 0.9 times to 1.1 times, the largest value or the smallest value. Even in this case, the linear portion can be emphasized with some accuracy.

The first image processing part 61 performs the first image processing using the pixel different from the first pixel Px1 in the target region of the captured image G1 as the first pixel Px1 when the first image processing by the first pixel group setting part 611, the first calculation part 612 and the first pixel value setting part 613 for a certain first pixel Px1 is finished. The first image processing part 61 performs the first image processing for each pixel included in the target region.

Further, the first pixel group setting part 611 and the first calculation part 612 may fix the first angle θ1, and calculate a first candidate pixel value by the one-dimensional filter in the direction corresponding to the first angle θ1 for each of the first pixels Px1 of the target region. After that, the first pixel group setting part 611 and the first calculation part 612 change the first angle θ1 and fix it again, and similarly calculate the first candidate pixel value of each of the first pixels Px1. After this processing is repeated and the first candidate pixel value is calculated for each of the first angles θ1 and each of the first pixels Px1, the first pixel value setting part 613 can calculate the pixel value of the second pixel corresponding to each of the first pixels Px1. In this way, a calculation sequence or the like is not particularly limited as long as the pixel value of the second pixel corresponding to each of the pixels Px of the setting region can be calculated.

The second image processing part 62 of the data processing part 51 performs image processing with respect to the captured image data corresponding to the captured image G1, and generates two-dimensional smoothing image data corresponding to two-dimensional smoothing image. Hereinafter, the image processing by the second image processing part 62 is referred to as second image processing. Here, the two-dimensional smoothing image is an image obtained by performing smoothing processing on the captured image G1 using a two-dimensional filter corresponding to the pixels disposed along in at least two directions. In the two-dimensional filter, the pixel number arranged in one direction is preferably two times or less the pixel number arranged in the other direction. The second image processing part 62 sets the pixel value of the two-dimensional smoothing image corresponding to each pixel in the captured image G1. Hereinafter, the pixel in the two-dimensional smoothing image corresponding to the first pixel Px1 in the captured image G1 is referred to as a third pixel.

The second pixel group setting part 621 of the second image processing part 62 sets a plurality of second pixel groups corresponding to the first pixel Px1 of the captured image G1.

Figure 5:
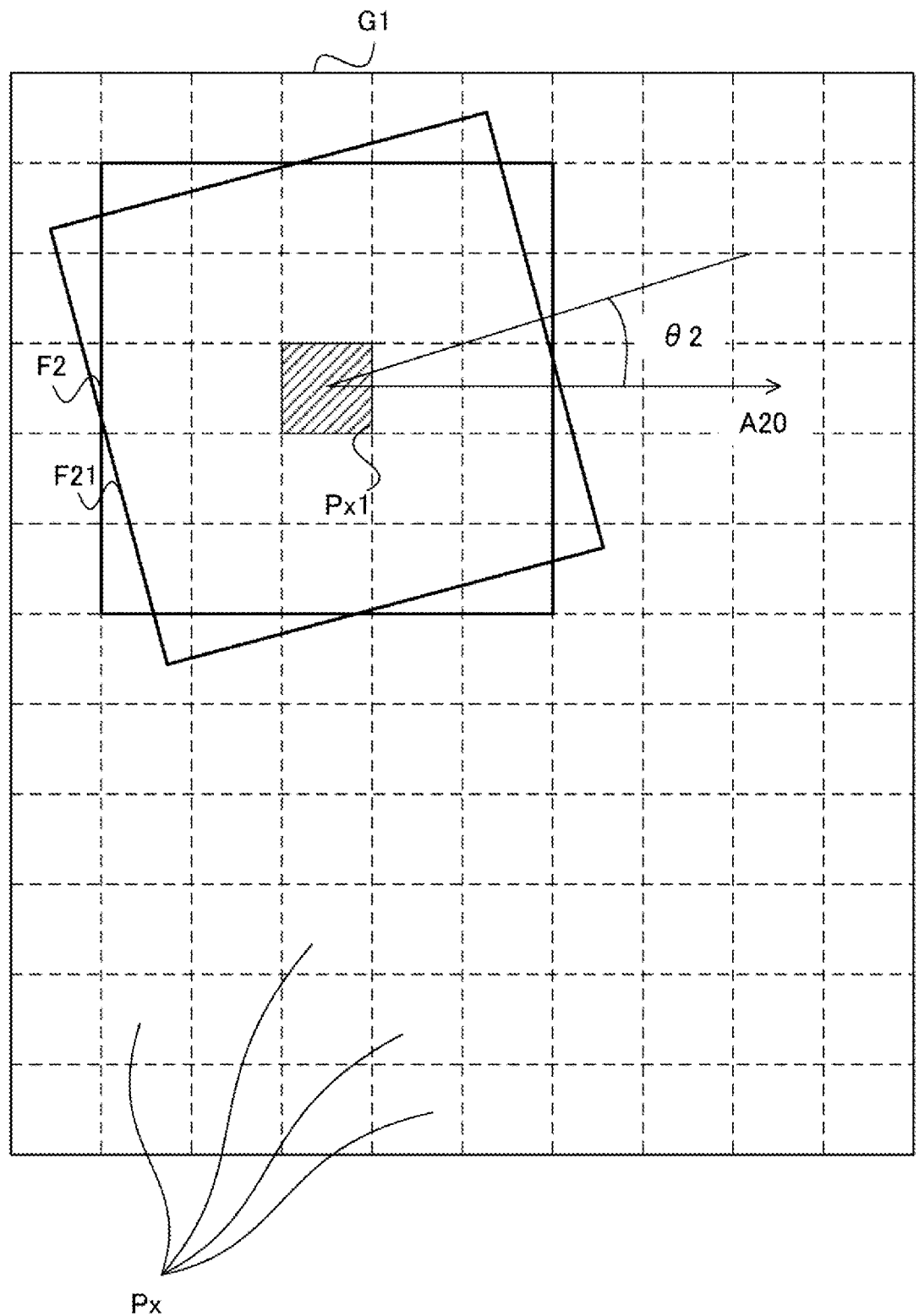
FIG. 5 is a conceptual view for describing second image processing according to the first embodiment.

FIG. 5 is a conceptual view for describing the second image processing. The second pixel group setting part 621 selects the first pixel Px1 from the pixels Px included in the captured image G1. The second pixel group setting part 621 selects and set the first pixel Px1 from the pixels included in the target region.

The second pixel group setting part 621 includes the first pixel Px1, and sets a pixel group, which corresponds to the two-dimensional filter obtained by moving (including rotating) a two-dimensional filter F2 by a predetermined angle in the reference direction, as a second pixel group Pg2. In other words, the second pixel group Pg2 is a pixel group in which the pixel group disposed along in at least two directions is disposed along in at least two directions obtained by rotating the at least two directions by a predetermined angle. The second pixel group setting part 621 sets the plurality of second pixel groups Pg2 for the plurality of predetermined angles, respectively. The predetermined angle is referred to as a second angle θ2 hereinafter. While the reference direction is the leftward/rightward direction of the captured image G1 in FIG. 5 (see an arrow A20), it is not particularly limited thereto. The reference direction may be any direction, or may be different from the reference direction in the above-mentioned first image processing.

In FIG. 5, the two-dimensional filter F2 (the second angle θ2=0°) and the two-dimensional filter F21 (the second angle θ2=about 20°) obtained by rotating the two-dimensional filter F2 about 20° are shown. In FIG. 5, the two-dimensional filter F2 corresponds to a square pixel block of vertical 5 pixels×horizontal 5 pixels, and the second pixel group Pg2 corresponding to the two-dimensional filter F2 includes 5×5 pixels about the first pixel Px1. A shape of the two-dimensional filter F2 corresponding to the second pixel group Pg2 is not particularly limited. The second pixel group Pg2 preferably includes a plurality of pixels adjacent to each other.

In FIG. 5, a partial region of the captured image G1 corresponding to the second pixel group Pg2 when the second angle θ2 is 0° and about 20° is schematically shown by the two-dimensional filter F2 and F21. When the second pixel group Pg2 corresponding to the two-dimensional filter F21 is set, the pixel or the like overlapping the two-dimensional filter F21 can be included in the second pixel group Pg2. However, in the pixels set in this way, since the shape of the pixel block corresponding to the second pixel group Pg2 varies, the accuracy decreases a little.

Accordingly, in actual calculation, the second pixel group setting part 621 preferably sets a plurality of pixels disposed about the pixel corresponding to the first pixel in at least two directions as the second pixel group Pg2 in the image obtained by rotating the captured image G1 in a direction that forms the second angle θ2 with respect to the reference direction. In the example of FIG. 5, the second pixel group setting part 621 rotates the captured image G1 by θ2 clockwise while fixing the two-dimensional filter F2, and sets pixels of vertical 5×horizontal 5 within a range of the two-dimensional filter F2 in the obtained image as the second pixel group Pg2. Accordingly, the second pixel group Pg2 corresponding to the two-dimensional filter F21 in the captured image G1 before rotation can be more accurately set than the case in which the two-dimensional filter F2 is rotated and the second pixel group Pg2 is set.

The second pixel group setting part 621 sets the second pixel groups Pg2 for the plurality of second angles θ2, respectively. The plurality of second angles θ2 are set multiple times for each predetermined angle selected from the range of, for example, 1° to 45° or the like. For example, the second pixel group setting part 621 can set the plurality of second angles θ2 from 0° to 179° by 1°, and set the second pixel group Pg2 for each of the second angles θ2.

The second calculation part 622 of the second image processing part 62 calculates a second candidate pixel value on the basis of the pixel value of the pixel included in the second pixel group Pg2. The second candidate pixel value is a value that is a candidate of the pixel value set as the third pixel corresponding to the first pixel Px1 in the second weighted image. In other words, the pixel value set as the third pixel is selected from the plurality of second candidate pixel values.

The second calculation part 622 calculates an average value of the pixel values of the pixels included in the second pixel group Pg2, and sets the average value as the second candidate pixel value. For example, the second calculation part 612 calculates an arithmetic mean of the pixel values of the 5×5 pixels corresponding to the two-dimensional filter F2, and sets the arithmetic mean as the second candidate pixel value of the second pixel group Pg2 corresponding to the two-dimensional filter F2. The second calculation part 622 calculates a second candidate pixel value for each of the second pixel groups Pg2 set by the second pixel group setting part 621. The second calculation part 622 calculates a second candidate pixel value for the second pixel group Pg2 corresponding to each of the plurality of second angles θ2. Further, the second calculation part 612 may calculate an average value of the pixel values of the pixels included in the second pixel group Pg2 as the second candidate pixel value according to the average other than the arithmetic mean, for example, a geometrical mean or the like. Alternatively, the second calculation part 622 can set a sum of the pixel values of the pixels included in the second pixel group Pg2 and a value obtained by appropriate adjustment of standardization or the like according to a numerical range that is settable using the sum as the pixel value as the second candidate pixel value. Like the above mentioned sum or the average, the calculation method of the second candidate pixel value set by the second calculation part 622 is not particularly limited as long as the second candidate pixel value can be set on the basis of the entire size of the pixel values of the pixels included in the second pixel group Pg2.

The second pixel value setting part 623 of the second image processing part 62 sets a pixel value of a third pixel in the two-dimensional smoothing image corresponding to the first pixel Px1 among the plurality of second candidate pixel values calculated for the first pixel Px1.

The second pixel value setting part 623 can set a pixel value of a third pixel corresponding to the largest value among the plurality of second candidate pixel values for the first pixel Px1. This means that, in the second image processing, in the two-dimensional filters F2 and F21 corresponding to the plurality of second angles θ2, the pixel value by the two-dimensional filter including the pixel having the highest pixel value as a whole is reflected in the two-dimensional smoothing image. As a result, when the luminance is increased as the pixel value is increased, smoothing that is not biased in a specific direction can be effectively performed. The second pixel value setting part 623 can set the pixel value of the third pixel corresponding to the smallest value in the plurality of second candidate pixel values for the first pixel Px1. Accordingly, when the luminance is increased as the pixel value is decreased, smoothing that is not biased to a specific direction can be effectively performed.

Further, the pixel value of the third pixel may be set as the value of a range of 0.8 times to 1.2 times the largest value or the smallest value, preferably a value of a range of 0.9 times to 1.1 times. Even in this case, smoothing that is not biased in a specific direction with some accuracy can be performed.

The second image processing part 62 performs the second image processing using the pixel different from the first pixel Px1 in the target region of the captured image G1 as the first pixel Px1 when the second image processing by the second pixel group setting part 621, the second calculation part 622 and the second pixel value setting part 623 for the first pixel Px1 is terminated. The second image processing part 61 performs the second image processing for each pixel included in the target region.

Further, like the case of the second image processing, a calculation sequence or the like is not particularly limited as long as the pixel value of the third pixel corresponding to each of the pixels Px of the setting region can be calculated.

Returning to FIG. 2, the first removing part 64 removes at least a part of a non-linear portion in the first weighted image on the basis of the two-dimensional smoothing image data, and generates second weighted image data corresponding to the second weighted image. Here, "removal" indicates removing an element of the pixel value that does not contribute to showing the non-linear portion in the first weighted image. Specifically, the first removing part 64 can generate an image, which uses an absolute value of a difference obtained by subtracting the pixel value of the two-dimensional smoothing image from the pixel value of the first weighted image as the pixel value, as the second weighted image. Accordingly, the spread of the luminance with low direction dependence, noise, or the like, is removed from the first weighted image, and the second weighted image that is the weighted image in which the linear portion is further emphasized is obtained.

The binarization part 65 performs binarization of a pixel value by a plurality of thresholds that are appropriately different for each portion on the basis of the pixel value of the pixel included in each portion of the second weighted image with respect to the second weighted image. The binarization part 65 divides the second weighted image into a plurality of regions. These regions are referred to as split regions. The binarization part 65 calculates an average value according to an arithmetic mean or the like of the pixel value of the pixel included in the split region and a standard deviation of the pixel value for each split region. A threshold of the binarization by the binarization part 65 is referred to as a binarization threshold Th. The binarization part 65 calculates the binarization threshold Th for each split region by setting the average value as avg and the standard deviation as σ according to the following Equation (1).

$$Th = avg + \alpha \times \sigma \quad (1)$$

Here, α is an integer. By determining the binarization threshold Th on the basis of the average value or variation of the pixel value in each split region in this way, the linear portion can be more accurately emphasized throughout the entire image.

In the image obtained by the binarization, a portion corresponding to the neurite Nr and a portion not corresponding to the neurite Nr are distinguished by different values. The image is referred to as a detection result image, and the data corresponding to the detection result image are referred to as detection result image data. The binarization part 65 stores the detection result image data obtained by performing the binarization for the second weighted image data in the storage 43 or the like.

Further, the binarization part 65 may store the data obtained by performing the binarization for the first weighted image data as the detection result image data in the storage 43 or the like. In this case, there is no need to perform processing of the above-mentioned second image processing and the first removing part 64. Even when the processing by the second image processing and the first removing part 64 is not performed, this is because the linear portion can be emphasized with desired accuracy by the first image processing. In addition, the data processing part 51 can appropriately perform image processing of level correction or the like of removing a relatively dark portion in the image before the binarization processing by the binarization part 65.

The data processing part 51 can appropriately perform analysis such as detection of the cross or which cell the segment of the linear portion is connected to, or the like, while performing detection of the neurite Nr in the detection result image. Further, the data processing part 51 can perform analysis of the length or the like of the neurite Nr and evaluate a state or the like of the cell Ce that was cultivated or is being cultivated on the basis of the data obtained by the analysis.

Referring to FIG. 1, the output controller 52 generates an output image output to the output part 44 on the basis of the detection result image data and outputs the image to the output part 44. The output controller 52 displays the detection result image on the display monitor of the output part 44.

The device controller 53 of the controller 50 controls the respective parts of the cultivation part 100 (an arrow A2) on the basis of the input or the like from the input part 41. The device controller 53 executes control related to cell cultivation (for example, control of the cultivation room 10 in which a temperature or a humidity is managed, and control of the driving part 12), or executes imaging on the imaging part 20.

Figure 6:
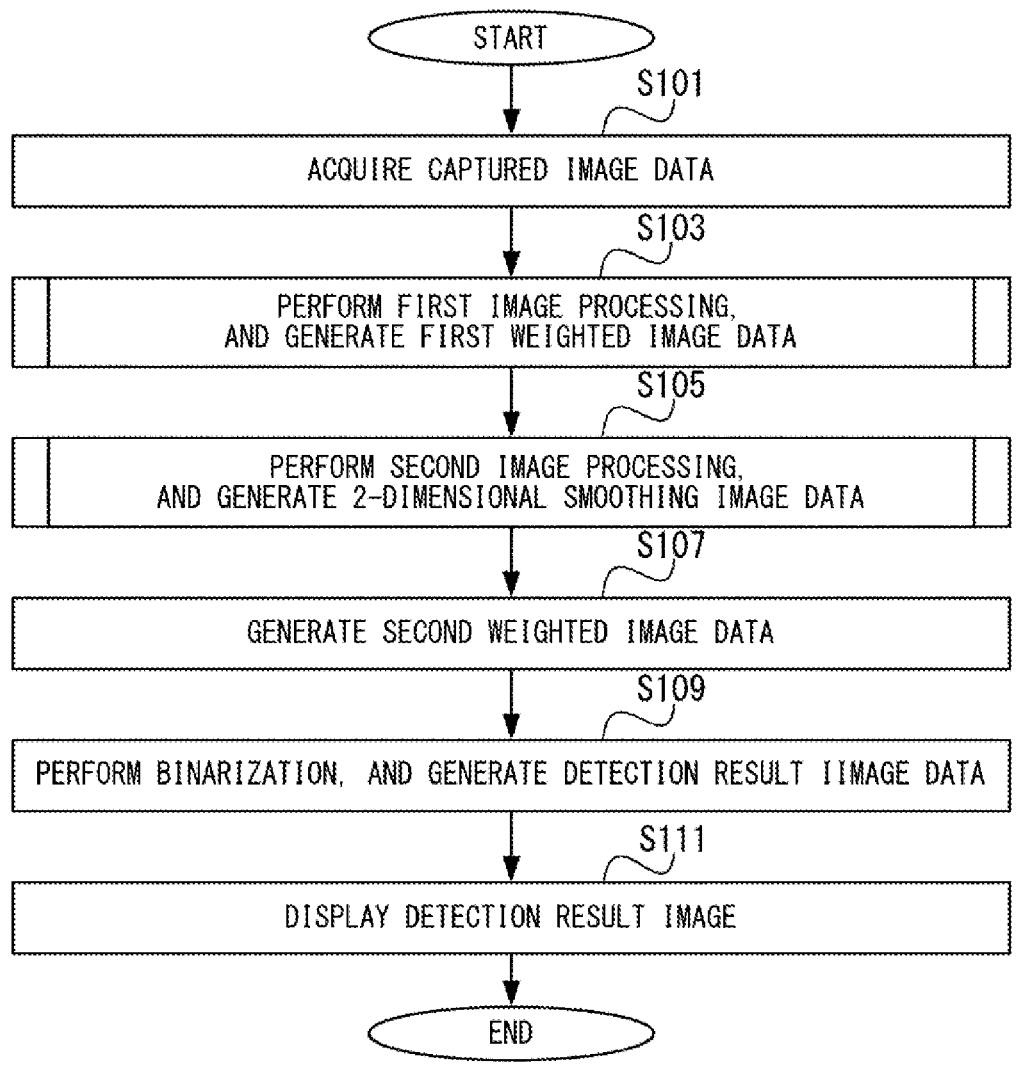
FIG. 6 is a flowchart showing a flow of an image processing method according to the first embodiment.

FIG. 6 is a flowchart showing a flow of an image processing method according to the embodiment. In step S101, the data processing part 51 acquires captured image data obtained by imaging of the imaging part 20. When step S101 is terminated, step S103 is started. In step S103, the first image processing part 61 performs first image processing on the captured image data, and generates first weighted image data. When step S103 is terminated, step S105 is started.

In step S105, the second image processing part 62 performs second image processing on the captured image data, and generates two-dimensional smoothing image data. When step S105 is terminated, step S107 is started. In step S107, the first removing part 64 generates the second weighted image data from the first weighted image data and the two-dimensional smoothing image data. When step S107 is terminated, step S109 is started.

In step S109, the binarization part 65 performs binarization on the second weighted image data, and generates detection result image data. When step S109 is terminated, step S111 is started. In step S111, the output controller 52 displays the detection result image on the output part 44. When step S111 is terminated, the processing is terminated.

Figure 7:
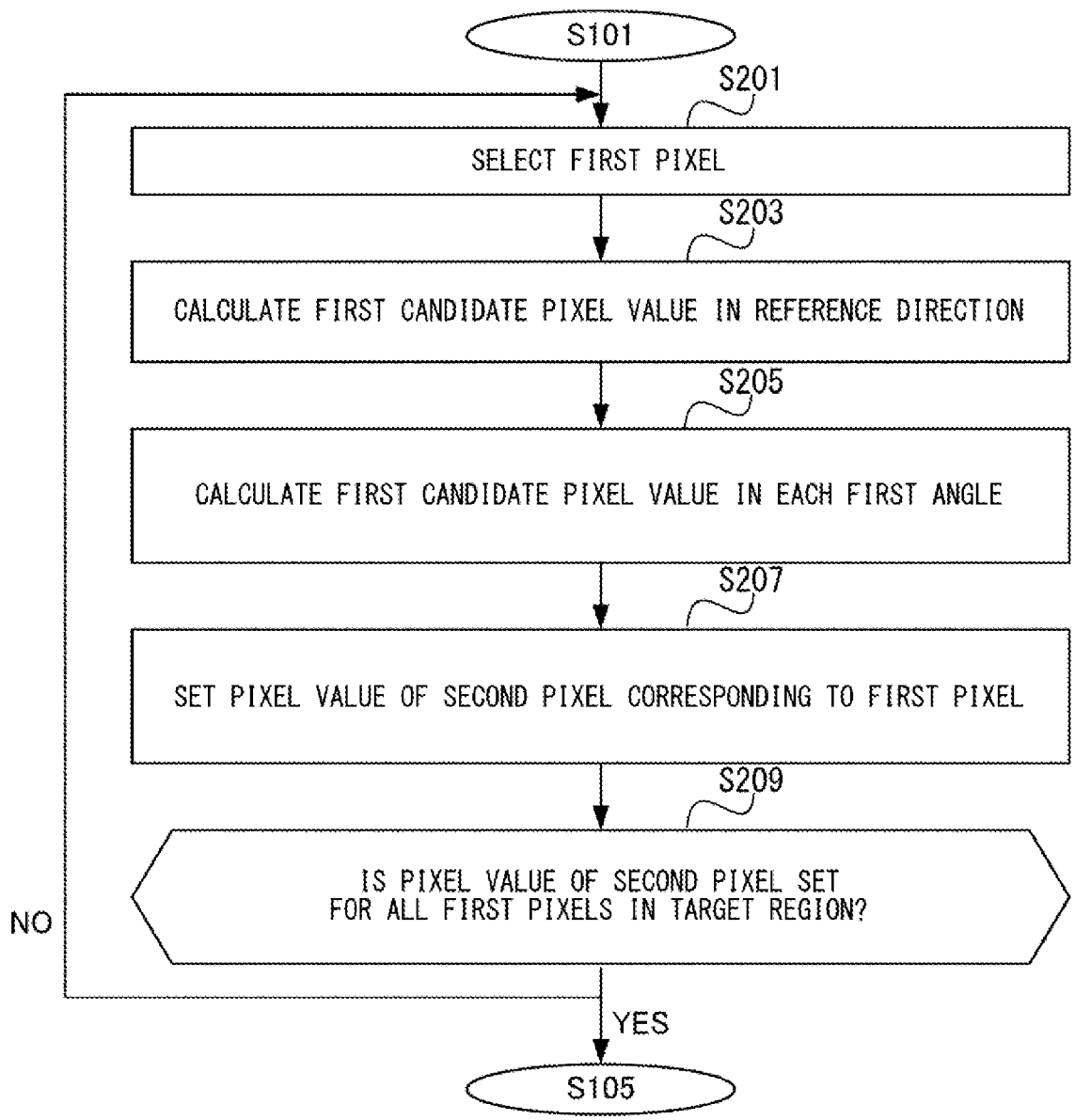
FIG. 7 is a flowchart showing a flow of first image processing according to the first embodiment.

FIG. 7 is a flowchart showing a flow of step S103 (first image processing) in the flowchart of FIG. 6. When step S101 is terminated, step S201 is started. In step S201, the first pixel group setting part 611 selects the first pixel Px1, to which the pixel value of the corresponding second pixel is not set, from the target region. When step S201 is terminated, step S203 is started.

In step S203, the first pixel group setting part 611 sets the first pixel group Pg1 included in the one-dimensional filter F1 extending in the reference direction, and the first calculation part 612 calculates a first candidate pixel value in the reference direction. When the step S203 is terminated, step S205 is started. In step S205, the first pixel group setting part 611 generates data obtained by rotating the one-dimensional filter or rotating the captured image and sets the first pixel group Pg1 for each of the first angles θ1, and the first calculation part 612 calculates a first candidate pixel value for each of the first angles θ1. When step S205 is terminated, step S207 is started.

In step S207, the first pixel value setting part 613 sets a pixel value of the second pixel corresponding to the first pixel Px1 from the first candidate pixel value for the first pixel Px1. When step S207 is terminated, step S209 is started.

Further, a sequence of steps S203, S205 and S207 may be appropriately changed.

In step S209, the data processing part 51 determines whether the pixel value of the second pixel corresponding to the first pixel Px1 is set for all the first pixels Px1 in the target region. The data processing part 51 makes a positive determination in step S209 when the pixel value of the second pixel corresponding to all the first pixels Px1 is set, and step S105 is started. The data processing part 51 makes a negative determination in step S209 and step S201 is started when there is the first pixel Px1 to which the pixel value of the corresponding second pixel is not set.

Figure 8:
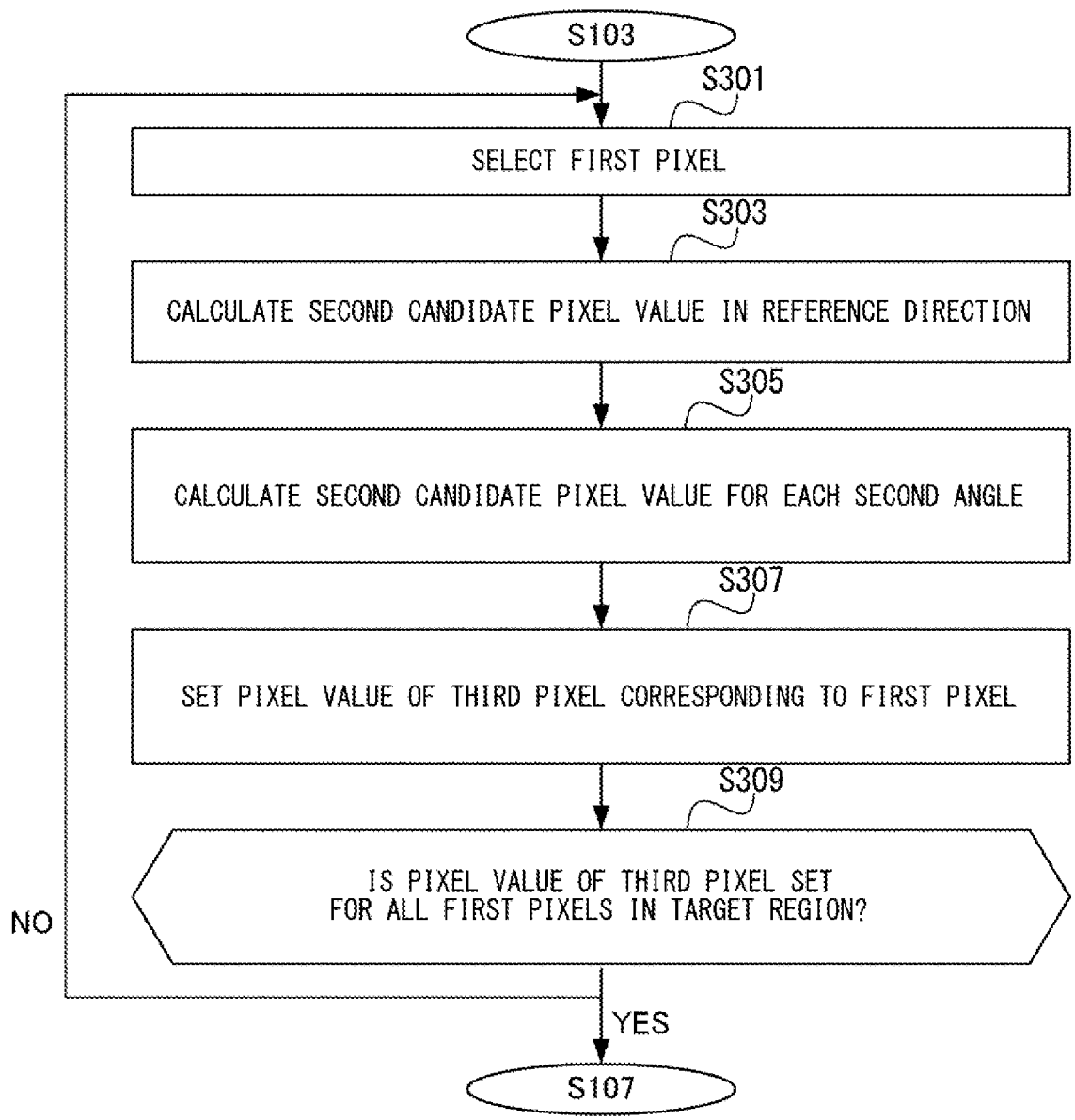
FIG. 8 is a flowchart showing a flow of second image processing according to the first embodiment.

FIG. 8 is a flowchart showing a flow of step S105 (second image processing) in the flowchart of FIG. 6. When step S101 is terminated, step S301 is started. In step S301, the second pixel group setting part 621 selects the first pixel Px1 to which a pixel value of the corresponding third pixel is not set from the target region. When step S301 is terminated, step S303 is started.

In step S303, the second pixel group setting part 621 sets the second pixel group Pg2 included in the two-dimensional filter F2 in the reference direction, and the second calculation part 622 calculates a second candidate pixel value in the reference direction. When step S303 is terminated, step S305 is started. In step S305, the second pixel group setting part 621 rotates the two-dimensional filter or generates data obtained by rotating the captured image and sets the second pixel group Pg2 for each of the second angles θ2, and the second calculation part 622 calculates a second candidate pixel value for each of the second angles θ2. When step S305 is terminated, step S307 is started.

In step S307, the second pixel value setting part 623 sets the pixel value of the third pixel corresponding to the first pixel Px1 from the second candidate pixel value for the first pixel Px1. When step S307 is terminated, step S309 is started.

Further, a sequence of steps S303, S305 and S307 may be appropriately changed.

In step S309, the data processing part 51 determines whether the pixel value of the third pixel corresponding to the first pixel Px1 is set for all the first pixels Px1 in the target region. The data processing part 51 makes a positive determination in step S309 when the pixel value of the corresponding third pixel is set for all the first pixels Px1, and step S107 is started. The data processing part 51 makes a negative determination in step S309 and step S301 is started when there is the first pixel Px1 to which the pixel value of the corresponding third pixel is not set.

According to the above-mentioned embodiment, the following effects are obtained.

(1) The image processing device 1 of the embodiment includes the first image processing part 61 configured to set a pixel value of a second pixel of a weighted image which is located at a position corresponding to the first pixel Px1 of the captured image G1 in the weighted image (second image) obtained through image processing of the captured image (first image) G1, and the first image processing part 61 includes the first pixel group setting part 611 configured to set the plurality of first pixel groups Pg1, which is set to correspond to the first pixel Px1 and which is disposed along in a plurality of directions that form a plurality of angles (the first angle 81) different from each other with respect to a predetermined direction (a reference direction of the image) in the captured image G1 or which is disposed along in a predetermined direction in each of the plurality of images obtained by rotating the captured image G1 by a plurality of angles (the first angle θ1) different from each other with respect to the predetermined direction (reference direction), the first calculation part 612 configured to calculate a plurality of first candidate pixel value on the basis of a size of the pixel value of the pixel included in each of the plurality of first pixel groups Pg1, and the first pixel value setting part 613 configured to set the pixel value of the second pixel of the weighted image on the basis of the plurality of first candidate pixel value. Accordingly, the linear portion of the cell in the image can be effectively emphasized.

(2) In the image processing device 1 of the embodiment, the first calculation part 612 can calculate the plurality of first candidate pixel values on the basis of the sum or average of the pixel value of the pixel included in each of the plurality of first pixel groups Pg1. Accordingly, it is possible to detect the direction in which the pixels with a high pixel value are arranged, and more effectively emphasize the linear portion in the image.

(3) In the image processing device 1 of the embodiment, the first calculation part 612 calculates the first candidate pixel value using smoothing filters F1, F11 and F12 for the first pixel group Pg1. Accordingly, it is possible to detect the linear portion on the basis of a length of the smoothing filter, and more effectively emphasize the linear portion in the image.

(4) In the image processing device 1 of the embodiment, the one-dimensional filters F1, F11 and F12 are one-dimensional smoothing filters. Accordingly, it is possible to detect the linear portion according to the shape (for example, a shape including a length, a width, or the like) of the one-dimensional filter, and more effectively emphasize the linear portion in the image.

(5) In the image processing device 1 of the embodiment, the first pixel setting part 611 configured to set the first pixel Px1 from the pixels that constitute the captured image G1 is provided, and the first pixel value setting part 611 can set a value of 0.8 times to 1.2 times the largest value or a value of 0.8 times to 1.2 times the smallest value among the plurality of first candidate pixel value as the pixel value of the second pixel. Accordingly, it is possible to detect the direction in which the pixels with a high or low pixel value are arranged, and more effectively emphasize the linear portion in the image.

(6) In the image processing device 1 of the embodiment, the second pixel group setting part 623 sets the plurality of second pixel groups Pg2 which is disposed along in at least two directions obtained by rotating at least two directions in which the pixels in the two-dimensional filter are arranged by a plurality of angles (the second angle θ2) different from each other with respect to the predetermined direction (reference direction) in the captured image G1 or which is disposed along in at least two directions in each of the captured images G1 rotated by a plurality of angles different with each other (the second angle θ2), the second image processing part 62 includes the second calculation part 622 configured to calculate the plurality of second candidate pixel values on the basis of the sum or average of the pixel values of the pixels included in each of the plurality of second pixel groups Pg1, and the second pixel value calculation unit 623 sets the pixel value of the third pixel on the basis of the plurality of second candidate pixel values. Accordingly, it is possible to generate the image data for removing the pixel values corresponding to a portion with low direction dependence in the subject.

(7) The image processing device 1 of the embodiment includes the first removing part 64 configured to remove at least a part of the non-linear portion in the weighted image on the basis of the two-dimensional smoothing image. Accordingly, it is possible to remove the pixel value corresponding to the portion with low direction dependence in the subject and further effectively emphasize the linear portion in the image.

(9) The image processing device 1 of the embodiment includes a binarization part 64 configured to perform binarization of the pixel values with respect to the weighted image according to a plurality of different binarization thresholds Th on the basis of the pixel values of the pixels included in the respective portions of the weighted image. Accordingly, it is possible to easily clearly show or easily analyze whether each pixel in the image corresponds to the linear portion through binarization.

(10) In the image processing device 1 of the embodiment, the captured image G1 is an image of the neurite Nr. Accordingly, it is possible to effectively emphasize the portion corresponding to the neurite Nr in the image. In addition, it is possible to more accurately perform analysis of the length or the like of the neurite Nr using the image in which the neurite Nr is emphasized.

(11) The imaging device according to the embodiment includes the above-mentioned image processing device 1, and the imaging part 20 configured to image the cell or the like including the linear portion. Accordingly, it is possible to effectively emphasize the linear portion in the captured image.

(12) The above-mentioned image processing device 1 that is the cultivation device according to the embodiment includes the cultivation part 100 configured to cultivate the cell. Accordingly, it is possible to effectively emphasize the linear portion in the image obtained by imaging the cell Ce cultivated in an undifferentiated or differentiated state.

(13) The image processing method according to the embodiment includes setting a pixel value of a second pixel of the captured image G1 located at a position corresponding to a first pixel Px1 of the captured image G1 in the weighted image (second image) obtained by image processing of the captured image (first image) G1, the setting of the pixel value of the second pixel includes setting the plurality of first pixel groups Pg1 which is set to correspond to the first pixel Px1, which is disposed along in a plurality of directions that form a plurality of angles (the first angle θ1) different from each other with respect to a predetermined direction (a reference direction) in the captured image G1 or which is disposed along in the predetermined direction in each of the plurality of images obtained by rotating the captured image G1 by the plurality of different angles (the first angle θ1), calculating a plurality of first candidate pixel values on the basis of a size of the pixel value of the pixel included in each of the plurality of first pixel groups Pg1, and setting the pixel value of the second pixel on the basis of the plurality of first candidate pixel values. Accordingly, it is possible to effectively emphasize the linear portion in the image.

The following modifications are also within the scope of the present invention, and can be combined with the above-mentioned embodiment. In the following variants, the parts showing the same structures and functions as the above-mentioned embodiment are referred to by the same reference signs, and description thereof will be omitted as appropriate.

(Variant 1)

In the second image processing of the above-mentioned embodiment, the second image processing part 62 may set the second candidate pixel value calculated from the pixel included in one of the two-dimensional filter as a pixel value of a third pixel without performing the processing of moving and rotating the two-dimensional filter or the captured image G1. Even in this case, this is because, if the two-dimensional filter has a shape with a small bias toward a specific direction, smoothing that is not biased in the specific direction can be performed with a certain degree of accuracy.

The image processing device 1 of the variant includes the second image processing part 62 configured to set the pixel value of the third pixel located at a position corresponding to the first pixel Px1 in the two-dimensional smoothing image obtained through image processing of the captured image G1, and the second image processing part 62 includes the second pixel group setting part 621 configured to set the second pixel group Pg2 including the pixel set to correspond to the first pixel Px1 and disposed along in at least two directions, and the second pixel value setting part 623 configured to set the pixel value of the third pixel on the basis of the sum or average of the pixel value of the pixel included in the second pixel group Pg2. Accordingly, it is possible to smooth the captured image G1 on the basis of the shape of the pixel block that constitutes the second pixel group Pg1 and effectively emphasize the linear portion in the image.

(Variant 2)

In the above-mentioned embodiment, the image processing device 1 may be configured to generate information of whether the first pixel Px1 in the captured image G1 corresponds to the linear portion using the one-dimensional filter. Hereinafter, the information is referred to as corresponding information of the pixel with respect to the linear portion (for example, the neurite Nr).

Figure 9:
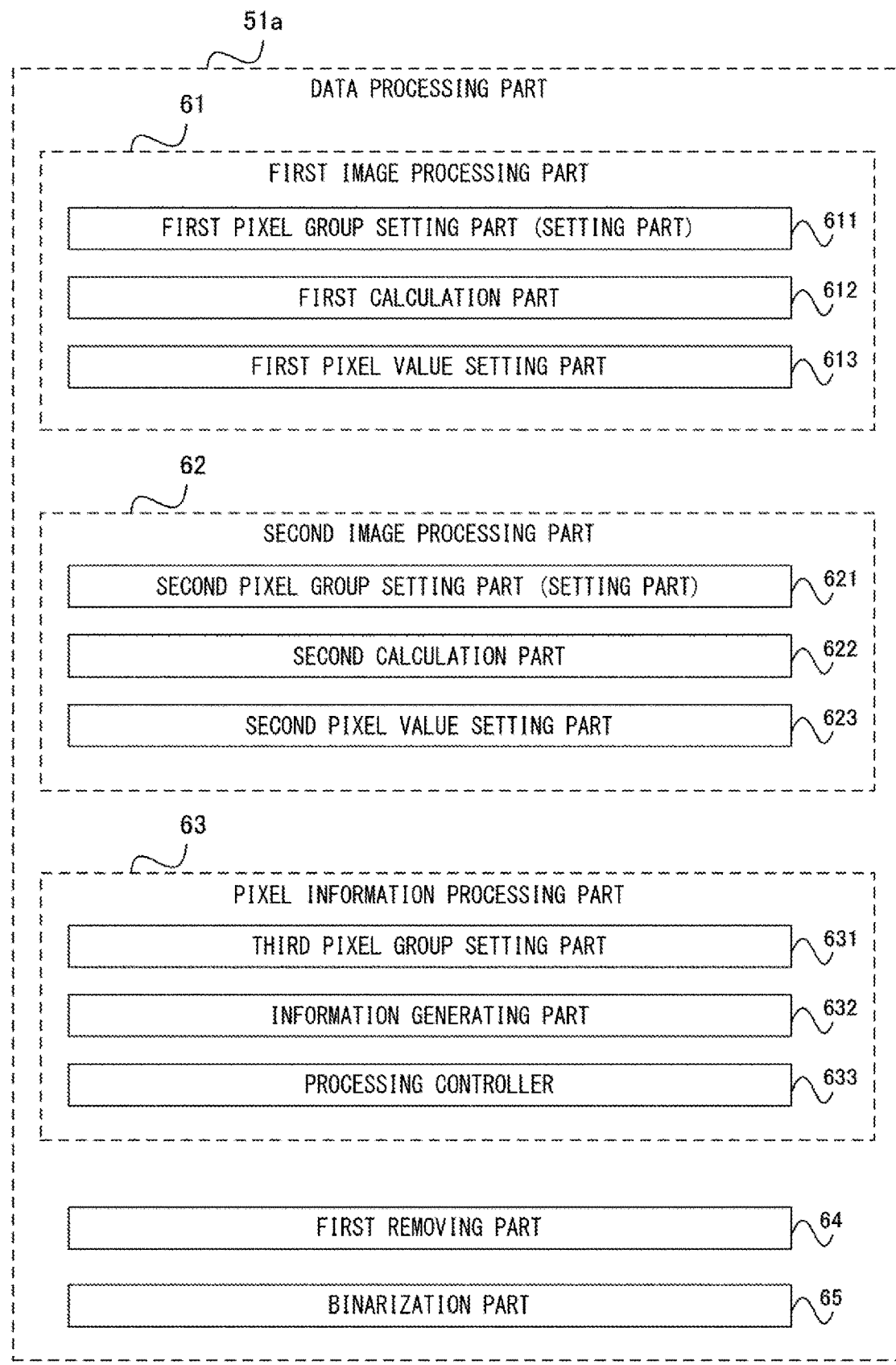
FIG. 9 is a conceptual view showing a configuration of a data processing part according to Variant 2.

FIG. 9 is a conceptual view showing a configuration of the data processing part 51a in the image processing device of the variant. The data processing part 51a is distinguished from the above-mentioned data processing part 51 in that a pixel information processing part 63 is provided.

The pixel information processing part 63 includes a third pixel group setting part 631, an information generating part 632, and a processing controller 633. The pixel information processing part 63 acquires information from the captured image data using the one-dimensional filter and processes the information.

The third pixel group setting part 631 sets a plurality of third pixel groups Pg3 corresponding to the first pixel Px1 in the captured image G1. Like the setting of the plurality of first pixel groups Pg1 by the above-mentioned first pixel group setting part 631, the third pixel group setting part 631 sets the plurality of third pixel groups Pg3 using the one-dimensional filters F1, F11 and F12 corresponding to the plurality of angles.

Figure 10:
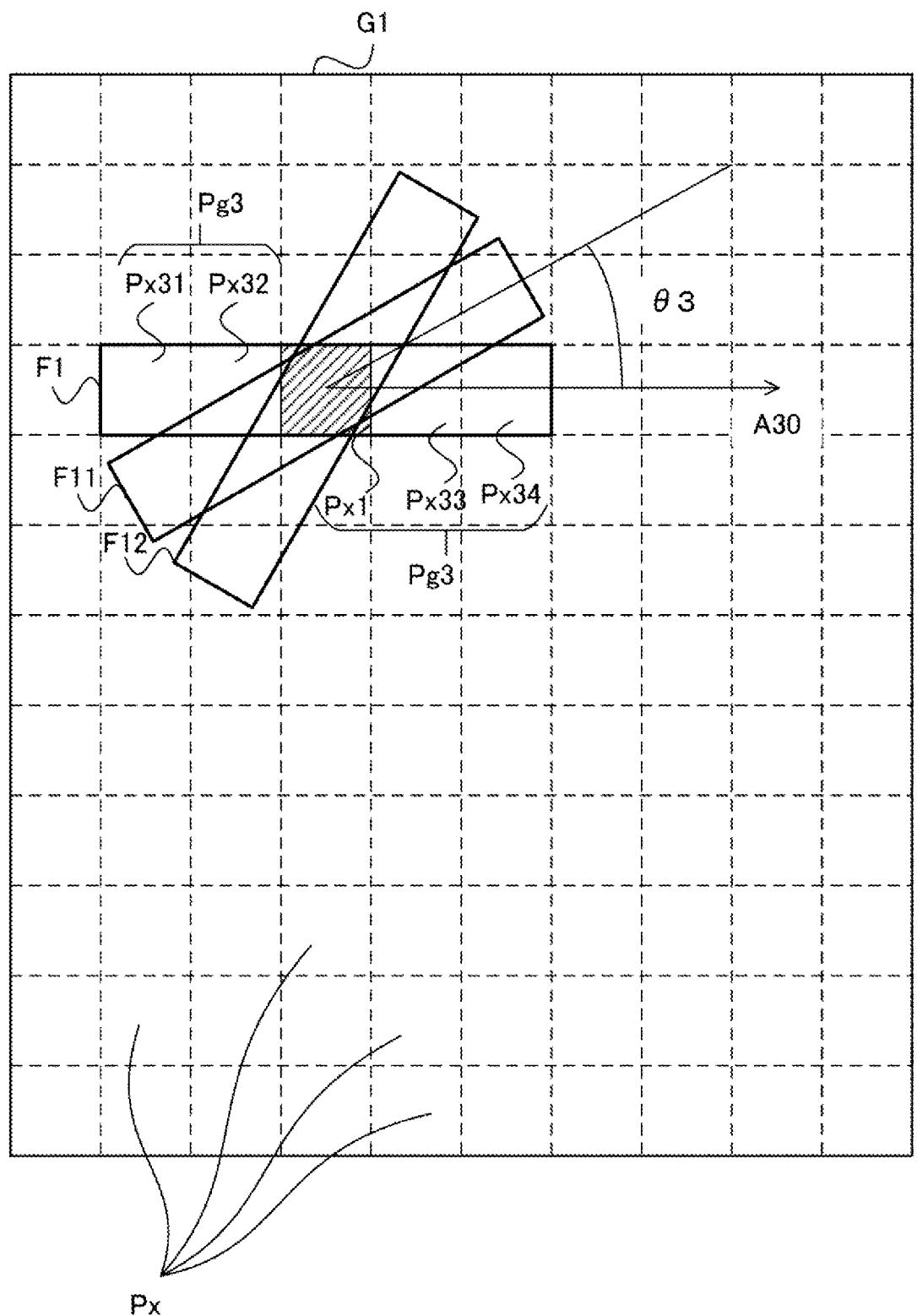
FIG. 10 is a conceptual view for describing first image processing according to Variant 2.

FIG. 10 is a conceptual view for describing the third pixel groups Pg3. The third pixel group setting part 631 selects the first pixel Px1 from the pixels Px included in the captured image G1. The third pixel group setting part 631 selects and sets the first pixel Px1 from the pixels included in the target region.

The third pixel group setting part 631 sets the pixel group including the first pixel Px1 and disposed along in the plurality of directions that form a predetermined angle with respect to the reference direction as the third pixel group Pg3. Hereinafter, the predetermined angle is referred to as a third angle $\theta 3$. While the reference direction is set as the leftward/rightward direction of the captured image G1 in FIG. 10 (see an arrow A30), it is not particularly limited and may be any direction. In FIG. 10, the plurality of pixels Px31, Px32, Px1, Px33 and Px34 included in the third pixel groups Pg3 when the third angles $\theta 3$ is 0° are shown. The third pixel groups Pg3 preferably include a plurality of pixels adjacent to each other in one direction in this way.

In actual calculation, the third pixel group setting part 631 preferably sets the plurality of pixels, which is disposed along the predetermined direction while having the pixel corresponding to the first pixel in the center, as the third pixel groups Pg3 in the image obtained by moving (including rotating in a direction that forms the third angles $\theta 3$ with respect to the reference direction) the captured image G1. The predetermined direction is not particularly limited and may be an arbitrary direction such as the reference direction or the like. Accordingly, it is possible to more accurately set the third pixel groups than the case in which the third pixel groups Pg3 are set by moving them (including rotating them to the one-dimensional filter F1).

The third pixel group setting part 631 sets the third pixel groups Pg3 for a plurality of third angles $\theta 3$, respectively. The plurality of third angles $\theta 3$ are set for each of the predetermined angle selected from a range of, for example, 1° to 45° or the like. For example, the third pixel group setting part 631 can set the plurality of third angles $\theta 3$ from 0° to 179° by 1°, and can set the third pixel groups Pg3 for each of the third angles $\theta 3$. The third pixel group setting part 631 sets the third pixel groups Pg3 for each of the first pixels Px1 of the target region.

The information generating part 632 generates the corresponding information. The information generating part 632 calculates a sum or an average of the pixel values, which is a value representing the entire size of the pixel values of the pixels included in each of the plurality of third pixel groups Pg3. The average can use an arithmetic mean or the like as appropriate. Hereinafter, the sum or average of the calculated pixel values is referred to as a one-dimensional filter value.

Figure 11:
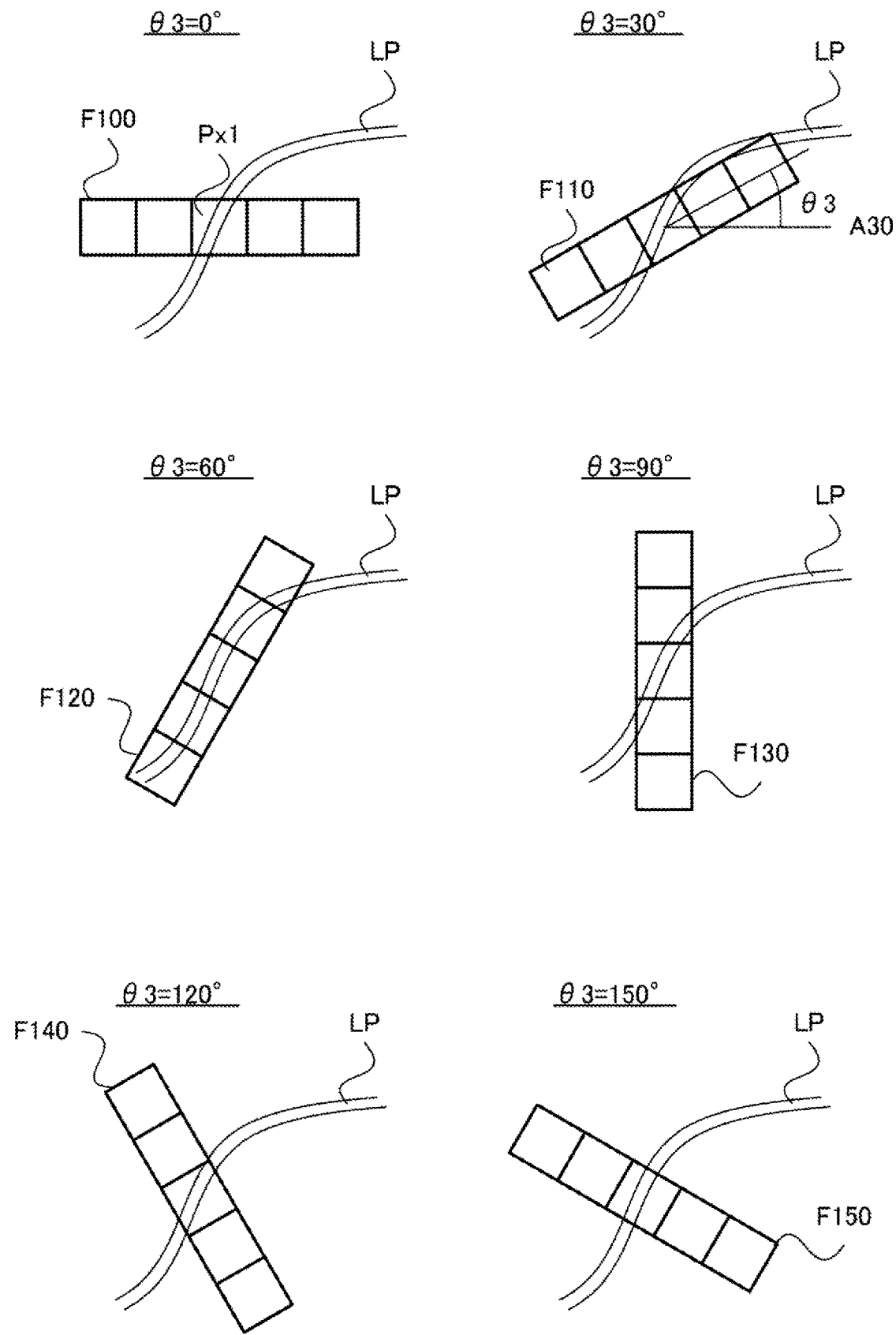
FIG. 11 is a conceptual view of a linear portion of an captured image and a position of a one-dimensional filter in each of cases in which an angle of the one-dimensional filter is 0°, 30°, 60°, 90°, 120° and 150°.

FIG. 11 is a conceptual view showing one-dimensional filters corresponding to the third angles $\theta 3$ and a linear portion LP for the plurality of third angles $\theta 3$. In FIG. 11, a one-dimensional filter F100 when the third angle $\theta 3$ is 0°, a one-dimensional filter F110 when the third angle $\theta 3$ is 30°, a one-dimensional filter F120 when the third angle $\theta 3$ is 60°, a one-dimensional filter F130 when the third angle $\theta 3$ is 90°, a one-dimensional filter F140 when the third angle $\theta 3$ is 120°, and a one-dimensional filter F150 when the third angle $\theta 3$ is 150° are shown.

In FIG. 11, since the first pixel Px1 is located on the linear portion LP, it is the pixel corresponding to the linear portion. As the light from the subject becomes stronger, when it is set as a high pixel value in the captured image data, the pixel value of the pixel corresponding to the linear portion LP is higher than the pixel value of the pixel that does not correspond to the linear portion. When the linear portion LP and the one-dimensional filter are disposed to overlap each other, the one-dimensional filter value that is the sum or average value of the pixel values of the pixels corresponding to the one-dimensional filter is highest.

In FIG. 11, when the third angles $\theta 3$ are 0°, 120° and 150°, overlapping between the one-dimensional filters F100, F140 and F150 and the linear portion LP is small, and the one-dimensional filter value is small in comparison with the case of the other third angles $\theta 3$. When the third angle $\theta 3$ is 30° or 90°, the one-dimensional filter F110 or the one-dimensional filter F130 and the linear portion LP overlap about 3 pixels in 5 pixels that constitute the one-dimensional filter. Accordingly, the -dimensional filter value is greater than the case in which the third angle $\theta 3$ is 0°, 120° or 150°. When the third angle $\theta 3$ is 60°, the one-dimensional filter F120 and the linear portion LP substantially overlap each other, and in the case shown in FIG. 11, the one-dimensional filter value is maximally increased.

The information generating part 632 generates data in which the third angle $\theta 3$ and the one-dimensional filter value correspond to each other. The data are referred to as filter value data hereinafter. The filter value data may be generated by performing smoothing or approximation by a curved line as appropriate. Accordingly, an influence of noise or the like can be reduced and accuracy can be increased.

Figure 12:
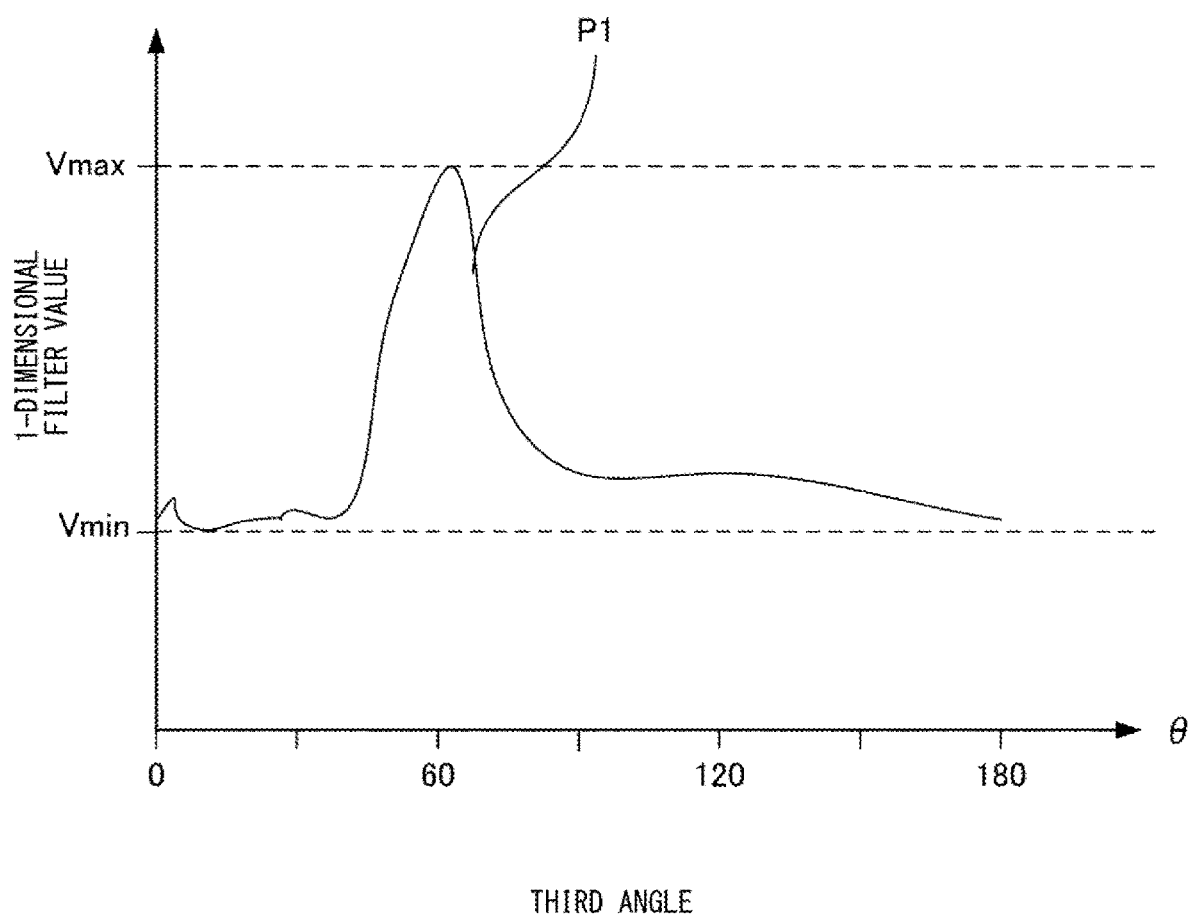
FIG. 12 is a graph showing an angle of the one-dimensional filter, and an average value of pixel values of a plurality of pixels corresponding to the filter.

FIG. 12 is a graph showing one-dimensional filter values with respect to the third angle $\theta 3$ in the first pixel Px1 that can be generated from the filter value data. FIG. 12 assumes that the one-dimensional filter value as shown in FIG. 11 has angle dependence. In the graph of FIG. 12, the one-dimensional filter value is a value from Vmin to Vmax, and the one-dimensional filter value is maximally increased when the third angle $\theta 3$ is about 60°. The information generating part 632 can calculate the third angle $\theta 3$ at which the one-dimensional filter value is maximally increased and a peak width of a peak P1 related to the third angle $\theta 3$. The information generating part 632 can detect a peak on the basis of whether a difference between Vmax and Vmin, an S/N ratio, or the like, is equal to or greater than the predetermined value.

Figure 13:
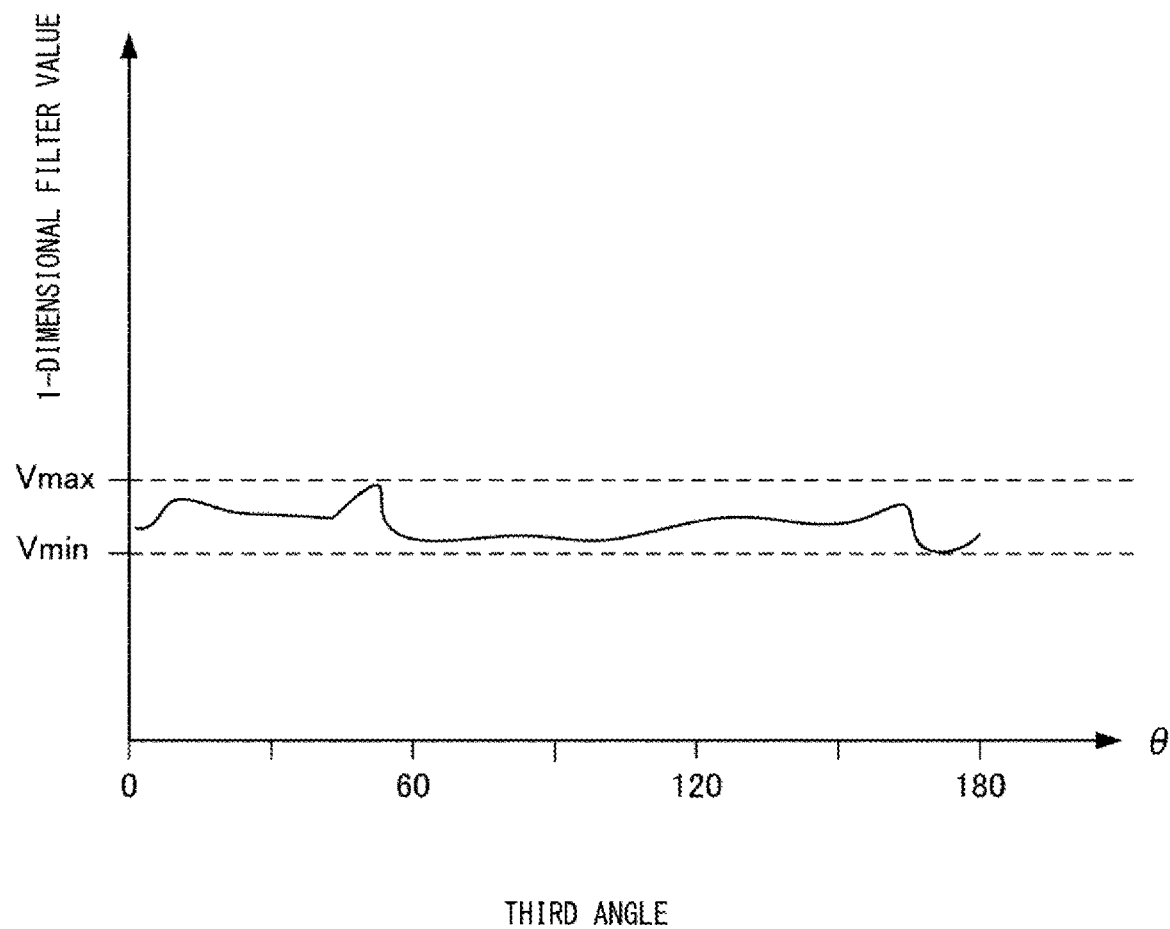
FIG. 13 is a graph showing an angle of the one-dimensional filter, and an average value of pixel values of a plurality of pixels corresponding to the filter.

FIG. 13 is a graph showing the one-dimensional filter value with respect to the third angle $\theta 3$ when there is no remarkable peak. In FIG. 13, since fluctuation of the one-dimensional filter value is smaller than that of the S/N ratio, the peak is not detected.

In the graph showing the one-dimensional filter value with respect to the third angle $\theta 3$, characteristics of the subject in the first pixel Px1 can be analyzed according to the number of peaks. When the number of peaks is 0, the first pixel Px1 is a portion that does not correspond to the line or cross. When the number of peaks is 1, the first pixel Px1 corresponds to the linear portion. When the number of peaks is 2, the first pixel Px1 corresponds to the cross. The information generating part 632 generates corresponding information of whether the first pixel Px1 corresponds to the linear portion through analysis of such a one-dimensional filter value. The information generating part 632 can generate corresponding information associated with each pixel by indicating in binary whether each pixel in the captured image corresponds to the linear portion, and store it in the storage 43 or the like. In addition, the information generating part 632 may also similarly generate information of whether each pixel in the captured image corresponds to the cross.

The information generating part 632 generates filter value data and corresponding information for each of the first pixels Px1 in the target region.

Further, in calculation of the one-dimensional filter value, first, the third pixel group setting part 631 can set the third pixel groups Pg3 by increasing an interval between the plurality of third angles θ3, and set the third pixel groups Pg3 by reducing the peak and the interval between the third angles θ3 adjacent thereto when the peak is detected. Accordingly, the information generating part 632 can accurately calculate the peak and the one-dimensional filter value adjacent thereto, and efficiently analyze the angle dependence of the one-dimensional filter value.

The processing controller 633 (FIG. 9) controls the processing of setting the first pixel group Pg1 of the first pixel group setting part 611 on the basis of the corresponding information. The processing controller 633 changes the number of the third angles θ3 set in the first image processing according to the position of the first pixel Px1 on the basis of the corresponding information. The processing controller 633 can reduce the number of the third angles θ3, which are set, to be smaller in the pixels that does not correspond to the linear portion than in the pixels corresponding to the linear portion. Alternatively, the processing controller 633 can set the first image processing such that it is not to be performed in the pixels that does not correspond to the linear portion. In other words, the processing controller 633 can set the first image processing such that the first pixel group setting part 611 selects the first pixel Px1 from the pixels corresponding to the linear portion. In this way, it is possible to more efficiently emphasize the linear portion in the image by setting the first image processing to be more accurately performed for the pixels corresponding to the linear portion.

Further, when the information generating part 632 generates information of whether each pixel in the captured image G1 corresponds to the cross, the processing controller 633 can appropriately set a condition of the first image processing on the basis of the information such that, for example, the first image processing is not performed in the pixel corresponding to the cross.

Figure 14:
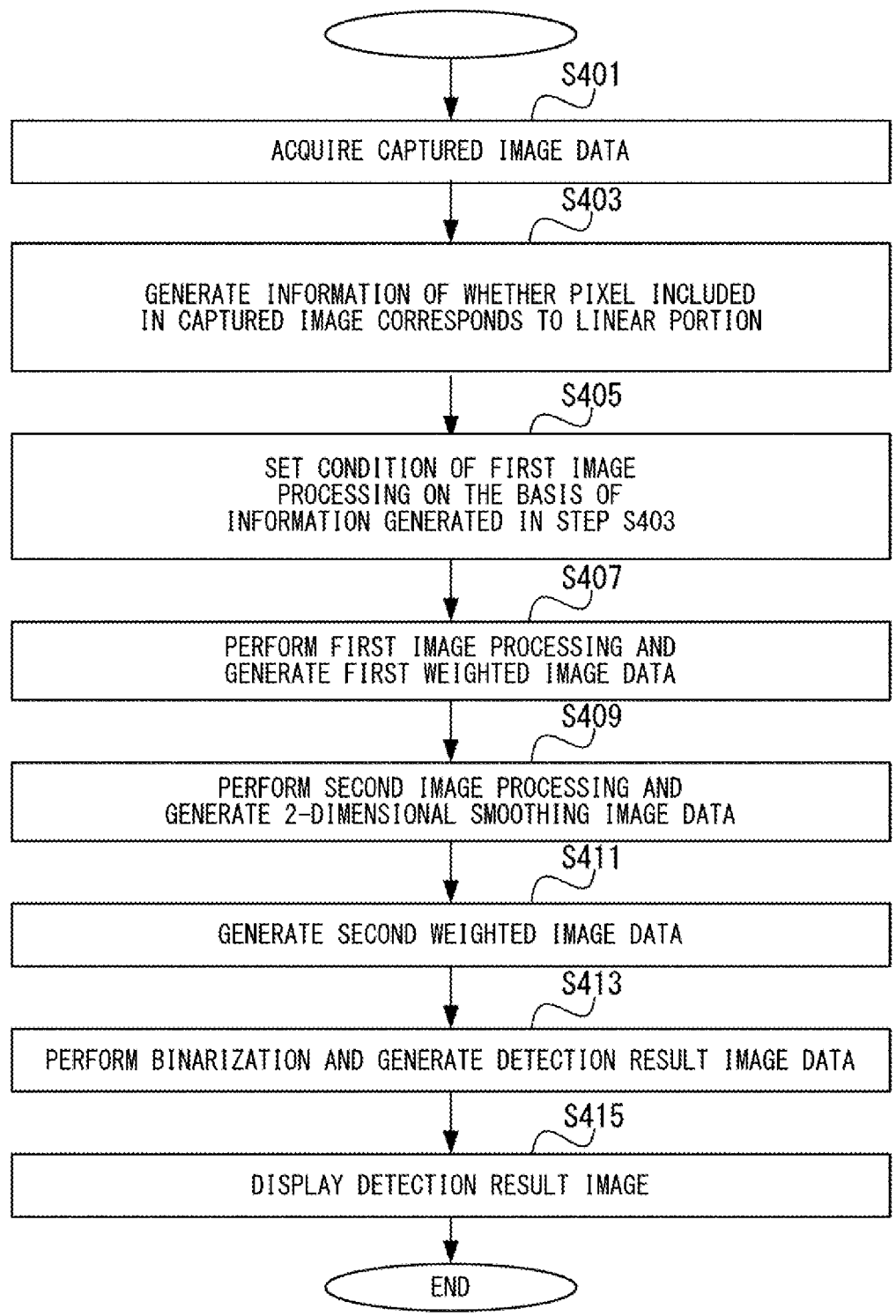
FIG. 14 is a flowchart showing a flow of an image processing method according to Variant 2.

FIG. 14 is a flowchart showing a flow of the image processing method of the variant. Since step S401 corresponds to step S101 of the flowchart of FIG. 6, description thereof will be omitted. When step S401 is terminated, step S403 is started. In step S403, the information generating part 632 generates information (corresponding information) of whether the pixel included in the captured image G1 corresponds to the linear portion. When step S403 is terminated, step S405 is started.

In step S405, the processing controller 633 sets a condition of the first image processing on the basis of the corresponding information generated in step S403. When step S405 is terminated, step S407 is started. In step S407, the first image processing part 61 performs the first image processing and generates first weighted image data on the basis of the condition set in step S403. When step S407 is terminated, step S409 is started. Since steps S409 to S415 correspond to steps 105 to S111 in the flowchart of FIG. 6, description thereof will be omitted.

(1) The image processing device of the variant includes the third pixel group setting part 631 configured to set the plurality of third pixel groups Pg3, which are the plurality of third pixel group Pg1 set to correspond to the first pixel Px1, disposed along in the plurality of directions that form the plurality of angles (the third angles θ3) with respect to the predetermined direction (reference direction) of the captured image (first image) G1 or arranged in the predetermined direction in each of the plurality of images obtained by rotating the captured image G1 by the plurality of angles (the third angles θ3), and the information generating part 632 configured to generate the information (corresponding information) of whether the first pixel Px1 corresponds to the linear portion in the captured image G1 on the basis of the sum or average of the pixel values of the pixels included in each of the plurality of third pixel groups Pg3. Accordingly, it is possible to more efficiently perform the image processing using the generated information.

(2) The image processing device of the variant includes the processing controller configured to control the processing of setting the first pixel group Pg1 of the first pixel group setting part 611 on the basis of the corresponding information generated by the information generating part 632. Accordingly, it is possible to more efficiently perform the first image processing using the generated information.

(3) In the image processing device of the variant, the number of the plurality of angles (the first angles θ1) when the first pixel group setting part 611 sets the plurality of first pixel groups Pg1 differs according to the position of the first pixel Px1, and the processing controller 633 sets the number at each position of the captured image G1 on the basis of the corresponding information. Accordingly, it is possible to accurately control the first image processing according to the position in the captured image using the generated information.

(4) In the image processing device of the variant, the processing controller 633 can determine whether the first pixel group setting part 611 performs the processing of setting the first pixel group Pg1 at each position of the captured image G1 on the basis of the corresponding information. Accordingly, it is possible to further more efficiently perform the first image processing using the generated information.

Further, the data processing part 51*a* may be configured to include a second removing part configured to remove at least a part of a non-linear portion in the first weighted image or the second weighted image on the basis of the corresponding information. The second removing part sets a pixel value as a value corresponding to the case in which there is no subject, for example, 0 for the pixel that does not correspond to the linear portion in the corresponding information. Accordingly, it is possible to further more emphasize the linear portion in the image.

(Variant 3)

In the above-mentioned embodiment, the target region may be configured such that the user performs setting via the input part 41.

Figure 15:
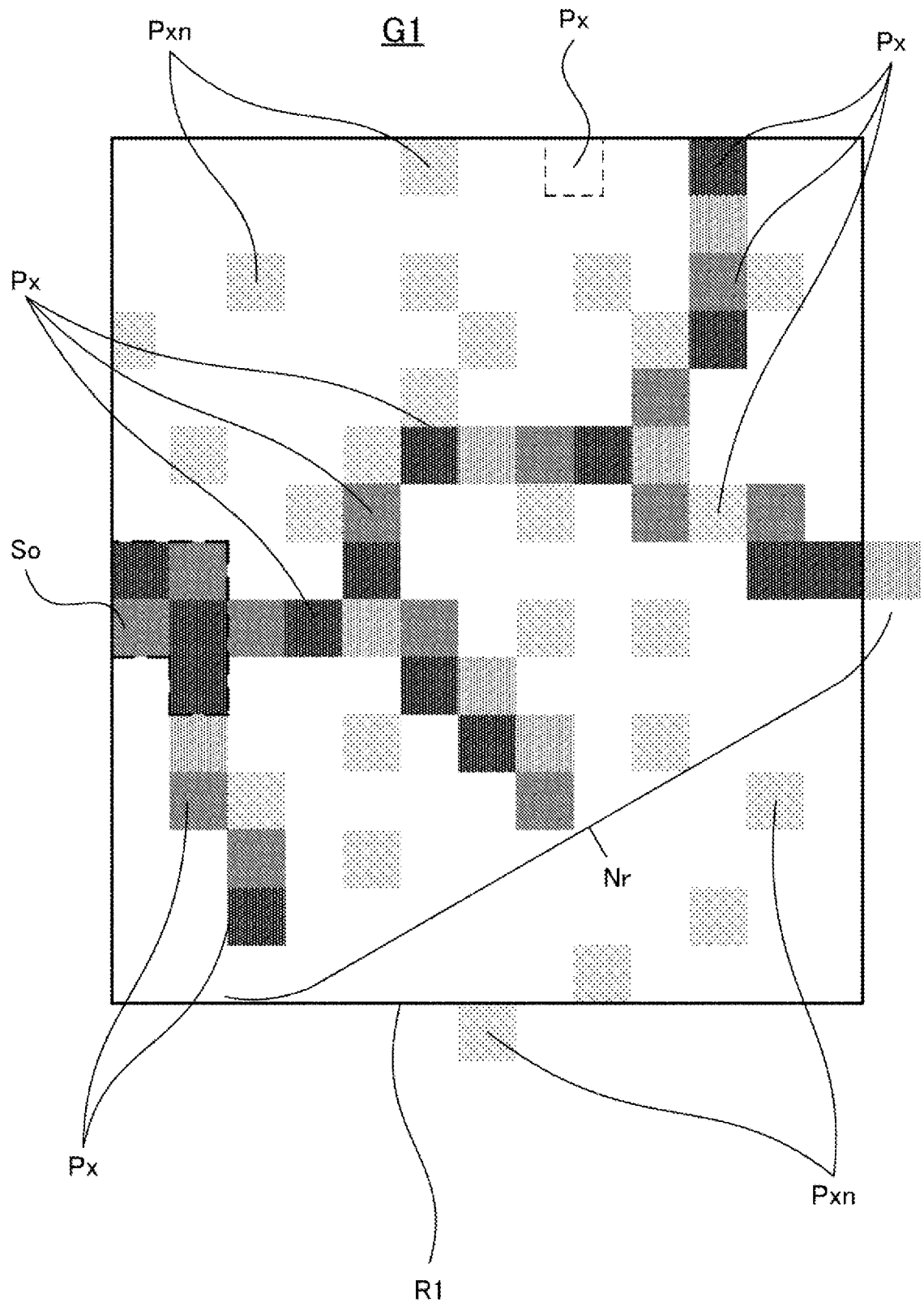
FIG. 15 is a conceptual view for describing setting of a range in which a first pixel is selected.

FIG. 15 is a conceptual view showing a target region R1. The user can input the range of the target region R1 by dragging, for example, a mouse as the input part 41 while observing a display screen of the output part 44 on which the captured image G1 is displayed.

The image processing device of the variant includes the input part 41 configured to input the position or range of the first pixel Px1 set as an object of the image processing by the first image processing part 61. Accordingly, it is possible to more efficiently emphasize the linear portion in the image as the user sets the object of the image processing.

(Variant 4)

While the subject of the captured image G1 has been described as the cell Ce and the linear portion to be emphasized has been described as the neurite Nr in the above-mentioned embodiment, the object to be emphasized is not limited to the example as long as the linear portion is included, and for example, may be a blood vessel. Further, it is more preferable that the subject of the captured image G1 is the eyeground, and the linear portion of the object to be emphasized is the blood vessel in the eyeground, and in particular, it is further preferable that the subject is a retina blood vessel or a choroid blood vessel.

In the image processing device of the variant, the captured image G1 is an image of the blood vessel. Accordingly, it is possible to effectively emphasize the linear portion in the image of the blood vessel.

(Variant 5)

In the above-mentioned embodiment, the display screen for the user to select and display at least one of the captured image G1 and the weighted image under the control of the output controller 52 may have a configuration which is output by the output part 44. The display screen is referred to as a first display screen. The weighted image may be referred to as a first weighted image or a second weighted image.

Figure 16:
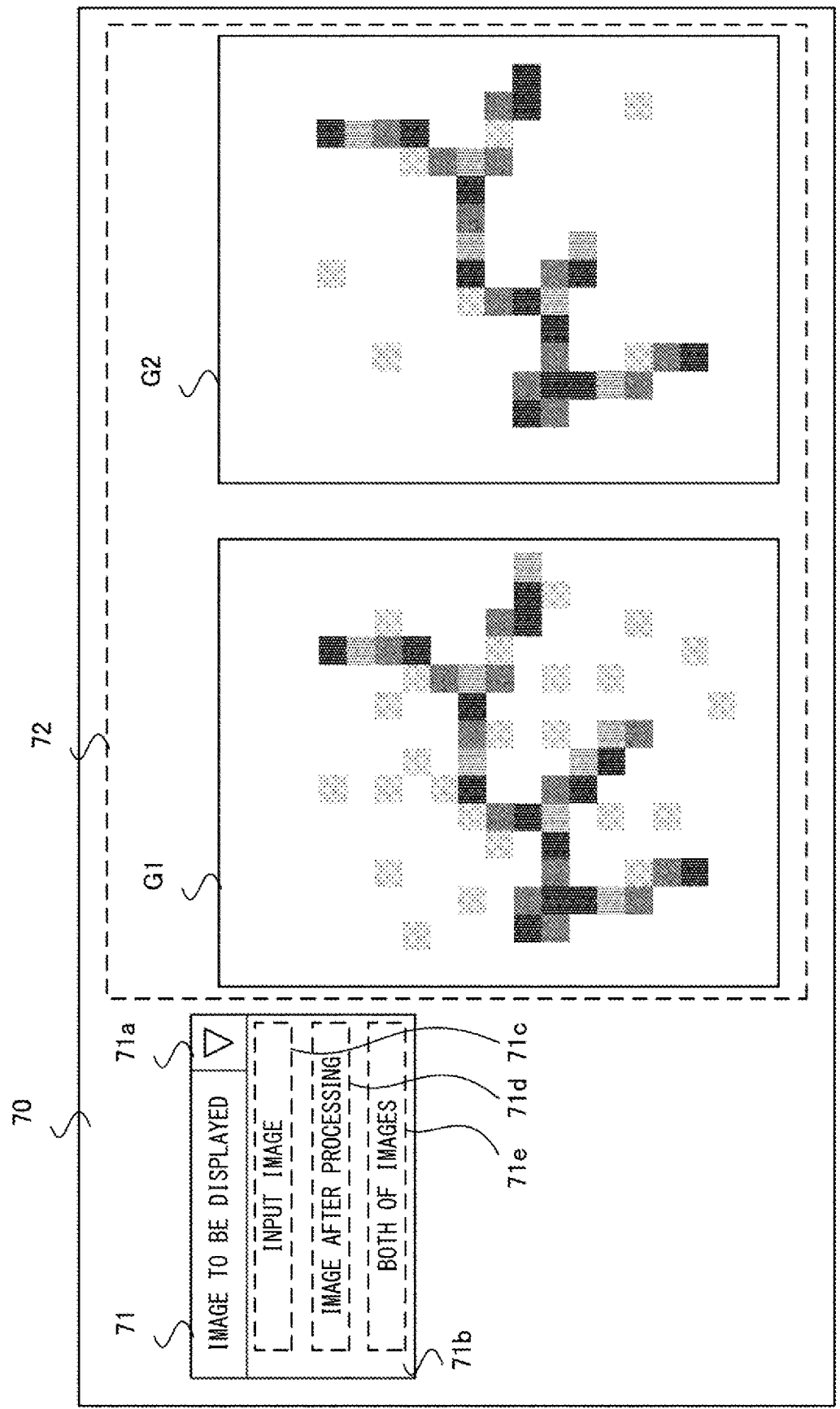
FIG. 16 is a conceptual view showing an example of a display screen configured to display a weighted image.

FIG. 16 is a conceptual view showing an example of a first display screen of the variant. A first display screen 70 includes an image selection unit 71, and a first image display unit 72 configured to display at least one of the captured image G1 and the weighted image. The image selection unit 71 is constituted by a combo box, and the combo box has a configuration in which display or non-display of a list 71*b* is switched whenever an icon 71*a* is selected. The list 71*b* includes a first input element 71*c*, a second input element 71*d*, and a third input element 71*e*. When the user clicks the first input element 71*c* using a mouse or the like, the captured image G1 that is an input image is displayed on the first image display unit 72, and a weighted image G2 is not displayed. When the user clicks the second input element 71*d*, the weighted image G2 is displayed on the first image display unit 72, and the captured image G1 is not displayed. When the user clicks the third input element 71*e*, the captured image G1 and the weighted image G2 are displayed on the first image display unit 72.

Further, the image selection unit 71 is not limited to the combo box and may be configured to include an arbitrary image element as long as an image to be displayed can be selected.

By selecting and displaying the captured image G1 or the weighted image G2 as appropriate by the user like the variant, the effect of the image processing method of the above-mentioned embodiment can be shown to the user in an easy-to-understand manner.

(Variant 6)

In the above-mentioned embodiment, the number of the plurality of first angles $\theta 1$ may be set by the user. The display screen configured to cause the user to set the number of the plurality of first angles $\theta 1$ under control of the output controller 52 may have a configuration which is output by the output part 44. The display screen is referred to as a second display screen.

Figure 17:
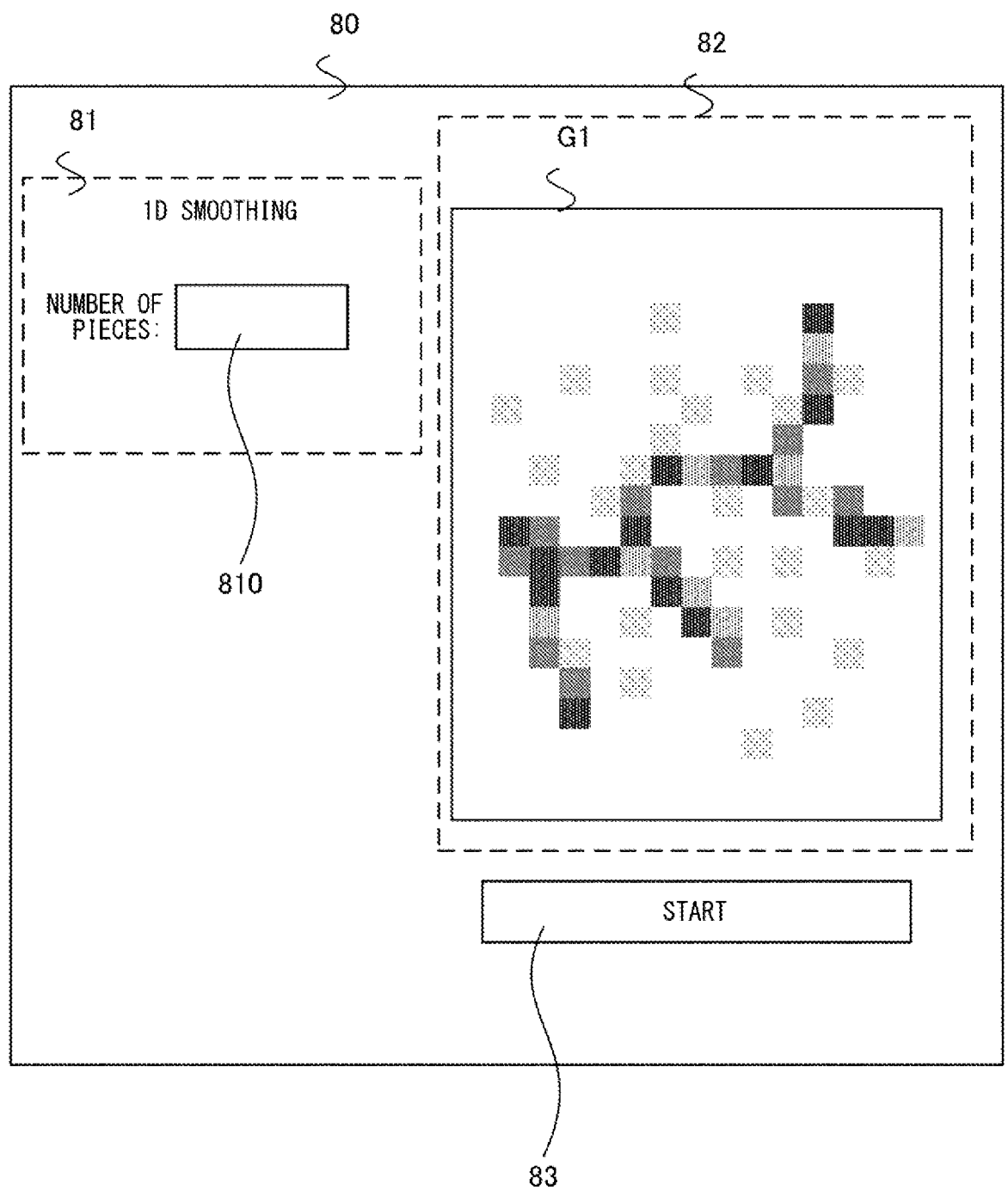
FIG. 17 is a conceptual view showing an example of a display screen configured to set a parameter.

FIG. 17 is a conceptual view showing an example of the second display screen of the variant. A second display screen 80 includes a first angle input part $\theta 1$, a second image display unit $\theta 2$ configured to display the captured image G1, and a first execution unit 83. The first angle input part $\theta 1$ includes a text box 810.

The first angle input part $\theta 1$ is an element configured to input the number of the first angle 81. The user can input a numerical value showing the number of the first angles $\theta 1$ on the text box 810 using a keyboard or the like. The user can perform the input while observing the captured image G1 displayed on the second image display unit 82 as appropriate.

Further, the image element for the input is not particularly limited to the text box and may be selected from the candidates of the displayed numerical values by the user as long as the number of the first angles $\theta 1$ can be input.

The first execution unit $\theta 3$ is a button configured to set the number of the first angles $\theta 1$ input by the user and cause the image processing device 1 to start the first image processing. When the first execution unit $\theta 3$ is clicked by the user, the first pixel group setting part 611 sets the plurality of first angles $\theta 1$ for each angle obtained by dividing, for example, 180° by the numerical number input into the text box 810, and performs the first image processing.

In the variant, as the user sets the parameter (setting information) for the first angle $\theta 1$ while observing the captured image G1 as appropriate, it is possible to more appropriately set the parameters.

Further, it is not limited to the case in which the number of the angles is input like the variant as long as the user can set the condition for the first angle $\theta 1$, the second angle $\theta 2$ or the third angles $\theta 3$.

(Variant 7)

In the above-mentioned embodiment, for the first image processing, the user can appropriately input or change the parameters for the first image processing by observing the display screen of the output part 44.

Figure 18:
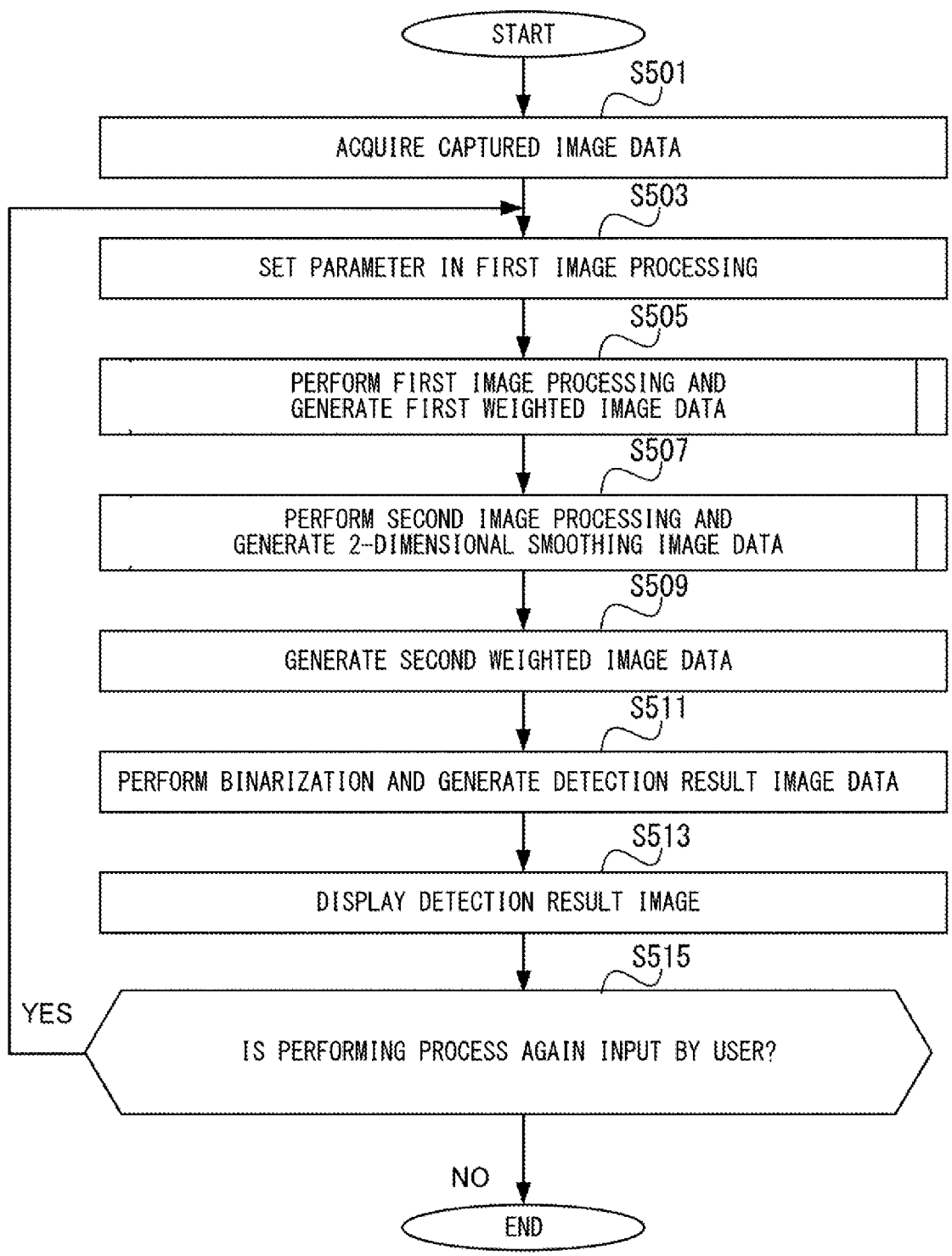
FIG. 18 is a flowchart showing a flow of an image processing method according to Variant 7.

FIG. 18 is a flowchart showing a flow of the image processing method of the variant. Since step S501 is the same as step S101 of the flowchart of FIG. 6, description thereof will be omitted. When step S501 is terminated, step S503 is started.

In step S503, the first image processing part 61 sets the parameters in the first image processing based on the input of the user. The parameters are referred to as first parameters. The first parameters may be numerical values indicating the lengths and widths of the one-dimensional filters F1, F11 and F12 in the first image processing. The user can input the first parameters while observing the detection result image when processing from the above-mentioned first image processing to the binarization is further already performed while observing the captured image G1. When step S503 is terminated, step S505 is started.

Further, the second image processing part 62 may be configured to set second parameters that are parameters in second image processing on the basis of input of the user. The second parameters may include, for example, numerical values indicating widths or shapes of the two-dimensional filters. Alternatively, the binarization part 65 may be configured to change a parameter (for example, a numerical value) such as a or the like of Equation (1) in binarization according to the above-mentioned embodiment based on the processing of the user. By appropriately setting the condition of the binarization in this way, it is possible to detect the linear portion such as the neurite Nr or the like accurately.

In step S505, the first image processing part 61 performs the first image processing and generates first weighted image data using the numerical values of the first parameters set in step S503. When step S505 is terminated, step S507 is started. Since steps S507 to step S513 correspond to steps S105 to S111 of the flowchart of FIG. 6, description thereof will be omitted. When step S513 is terminated, step S515 is started.

In step S515, the data processing part 51 determines whether an instruction of performing the processing related to the above-mentioned image processing method such as the first image processing or the like is input via the input part 41 by the user again. When the instruction is input, the data processing part 51 makes a positive determination in step S515, and step S503 is started. When the instruction is not input, the data processing part 51 makes a negative determination in step S515, the processing is terminated.

Hereinafter, in the image processing method of the variant, while the example of the display screen displayed on the output part 44 has been described, the aspect of the image in each display screen, and the shape of each display element such as a button, a text box, or the like, are not limited to as being shown in the following drawings.

Figure 19:
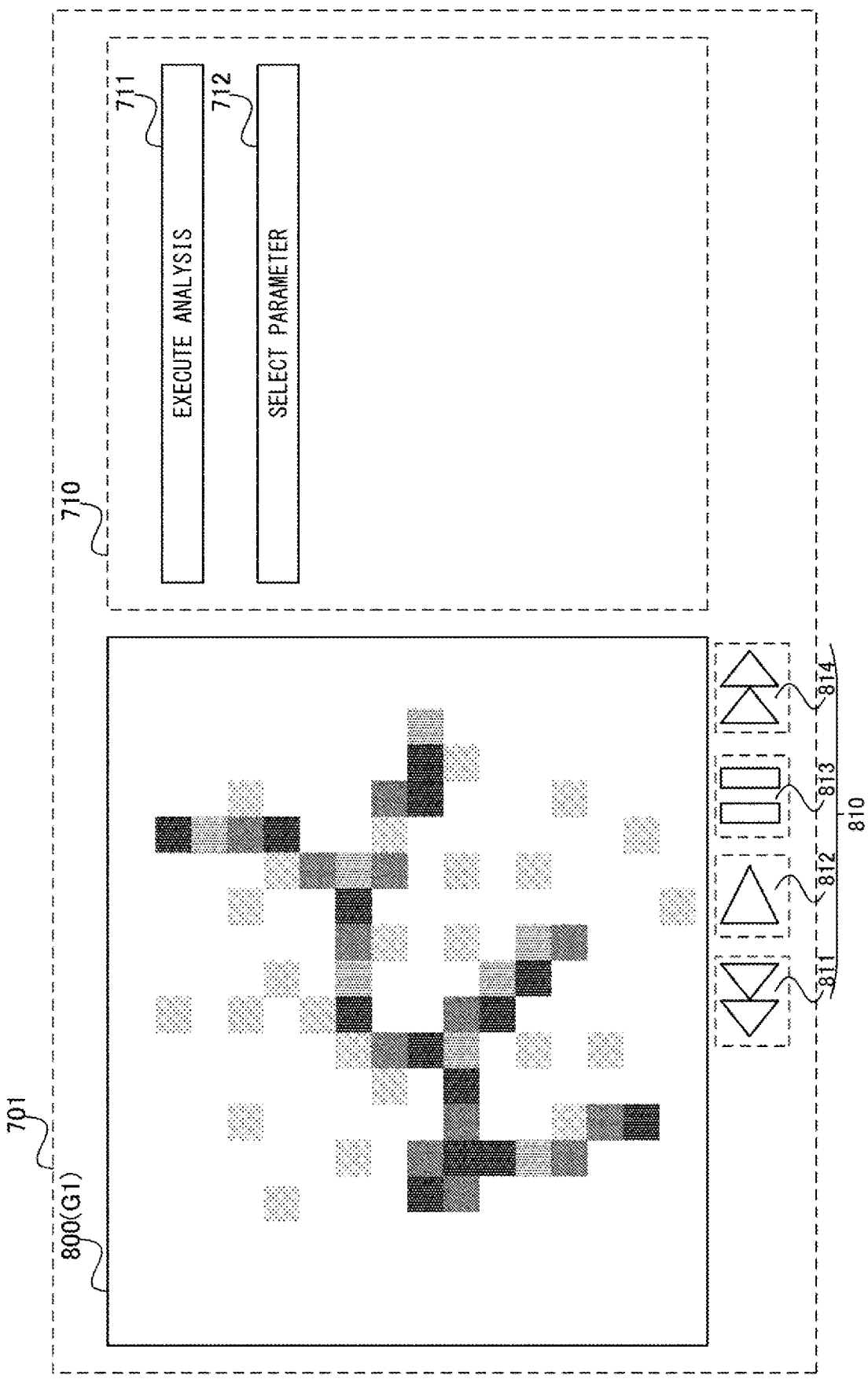
FIG. 19 is a conceptual view showing an example of a display screen according to Variant 7.

FIG. 19 is an example of a screen displayed on the output part 44 by the output controller 52 when the first parameter is selected, and the screen is a basic screen 701. The basic screen 701 includes an image display unit 800, a first input element display unit 710, and a video operation unit 810. The video operation unit 810 includes a rewinding button 811 configured to perform rewinding when a video is displayed on the image display unit 800, a reproduction button 812 configured to perform reproduction, a pause button 813 configured to perform a pause, and a fast forward button 814 configured to perform fast forward. While the captured image G1 is shown in the image display unit 800 of the basic screen 701 of FIG. 19, the image displayed on the image display unit 800 is changeable as appropriate.

The first input element display unit 710 includes an execution button 711 and a parameter selection button 712, which are input elements configured to cause the image processing device 1 to perform predetermined operations, as the user clicks with the cursor using the mouse, the touch pad, or the like.

The execution button 711 is an input element configured to cause the data processing part 51 to execute processing from first image processing to binarization and configured to shift the display screen to a result display screen that is a screen configured to display a detection result of the neurite Nr. When the execution button 711 is clicked, the output controller 52 displays a result display screen 702 of FIG. 21 on the output part 44. Here, when the user does not change the parameter, it is preferable to perform the first image processing using the first parameter that was preset.

The parameter selection button 712 is an input element configured to display a display element configured to input the first parameter. When the parameter selection button 712 is clicked by the user, a first text box 713 and a second text box 714 (FIG. 20) are displayed on the first input element display unit 710.

Figure 20:
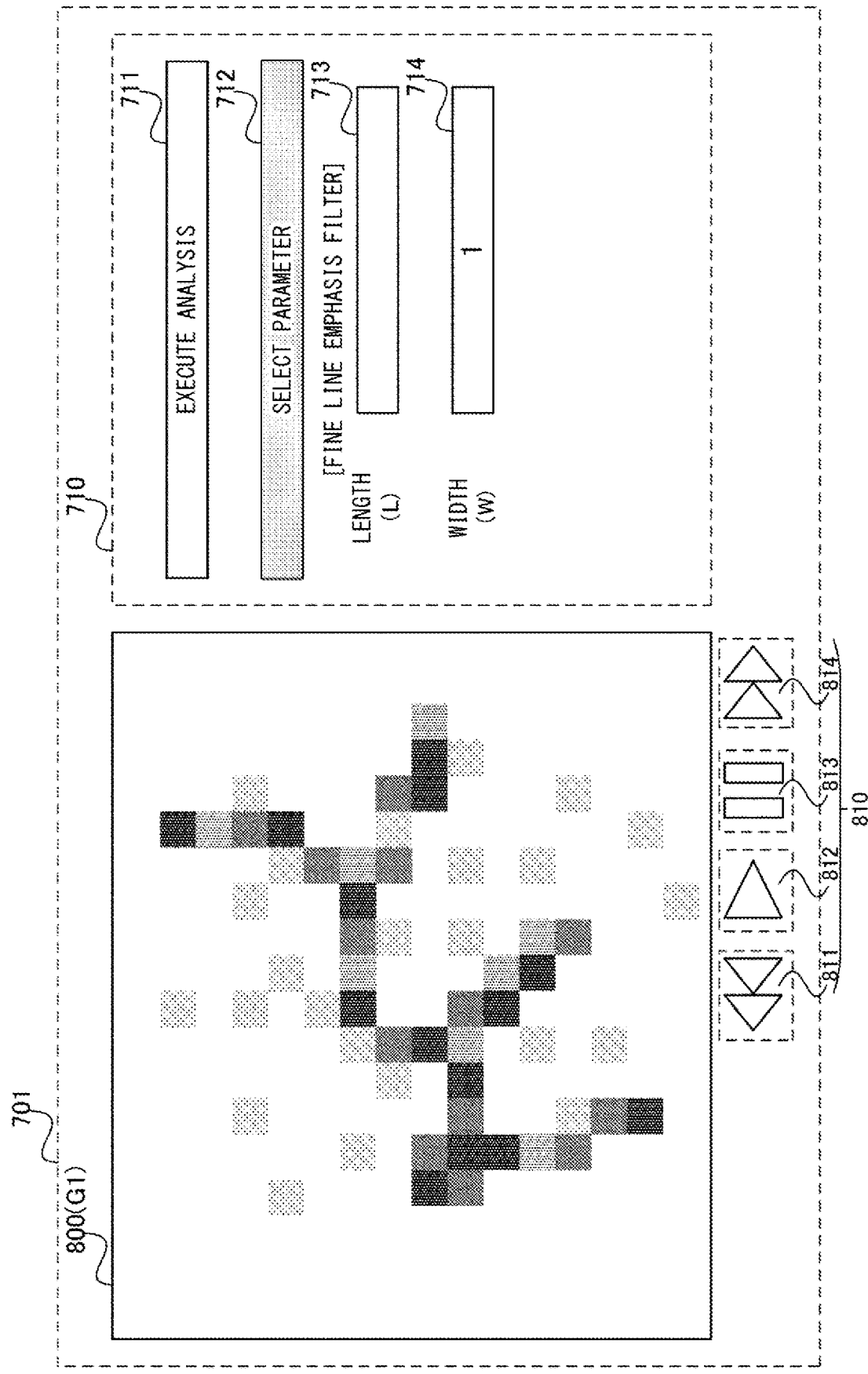
FIG. 20 is a conceptual view showing an example of the display screen according to Variant 7.

FIG. 20 is a conceptual view showing the first text box 713 and the second text box 714. In the basic screen 701 of FIG. 20, the first input element display unit 710 includes the first text box 713 and the second text box 714 into which numerical values can be input using a keyboard or the like by the user. The first text box 713 is configured such that the lengths of the one-dimensional filters F1, F11 and F12 can be input as the pixel numbers. The second text box 714 is configured such that the widths of the one-dimensional filters F1, F11 and F12 can be input as the pixel numbers.

When the first text box 713 and the second text box 714 are displayed, the parameter selection button 712 is displayed in an aspect different from when the first text box 713 and the second text box 714 are not displayed according to a change of a color phase, chroma, brightness, or the like. In FIG. 20, this point is shown by hatching the parameter selection button 712.

Further, the first text box 713 and the second text box 714 may be displayed from the beginning when the basic screen 701 is displayed.

Figure 21:
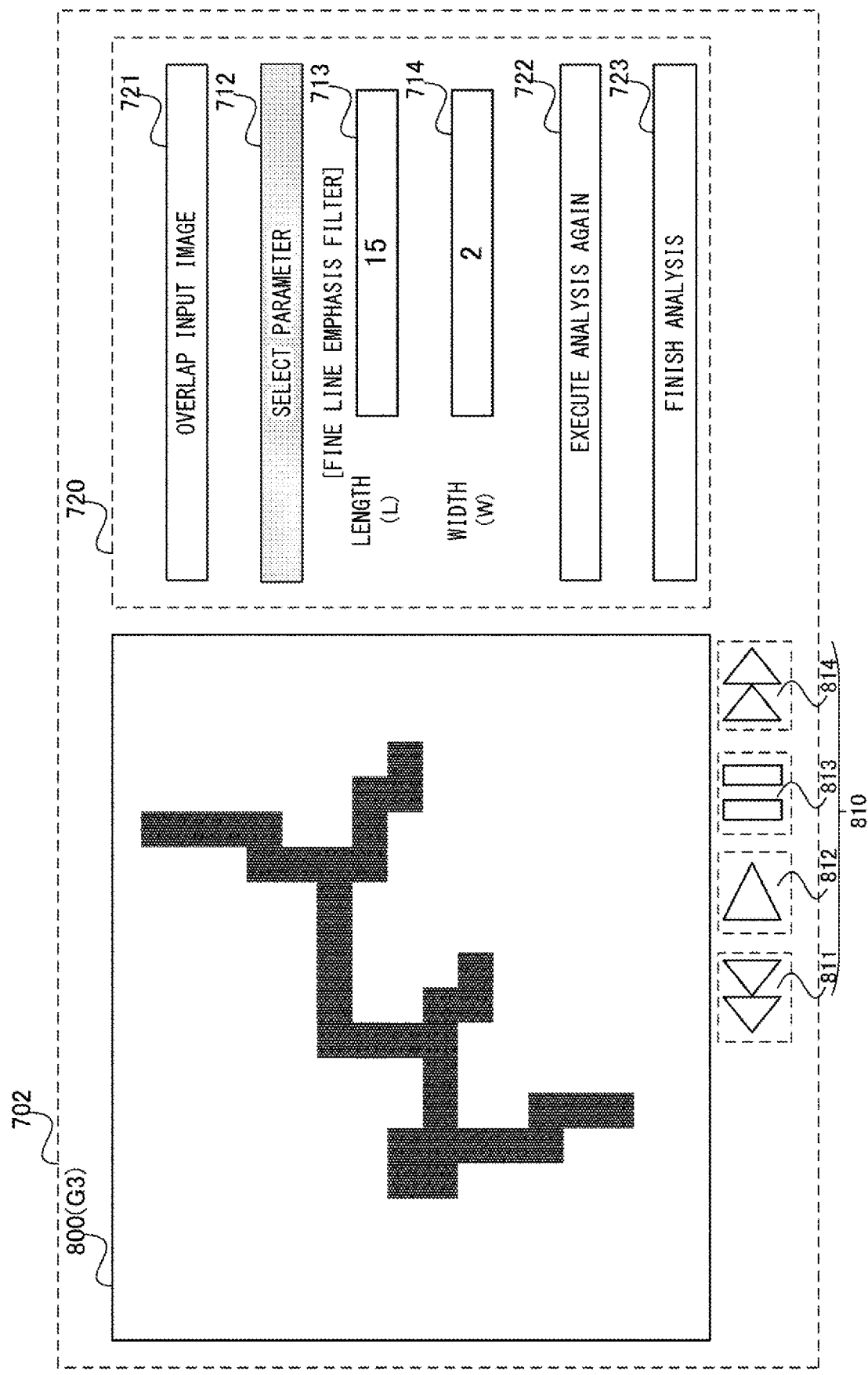
FIG. 21 is a conceptual view showing an example of the display screen according to Variant 7.

FIG. 21 is a conceptual view showing an example of a result display screen. The result display screen 702 is displayed on a display screen of the output part 44 by the output controller 52. The result display screen 702 includes the image display unit 800, a second input element display unit 720, and the video operation unit 810. A detection result image G3 is displayed on the image display unit 800 of FIG. 21.

The second input element display unit 720 includes an image overlapping button 721, a re-execution button 722 and an end button 723, which are input elements configured to cause the image processing device 1 to perform predetermined operations as the user clicks a cursor using a mouse, a touch pad, or the like.

Further, the above-mentioned parameter selection button 712 is displayed on the second input element display unit 720, and in the example of FIG. 21, the parameter selection button 712 is selected by the user, and the first text box 713 and the second text box 714 are displayed. In the result display screen 702, it is preferable to display the value set in the first image processing performed immediately before as initial setting values of the first text box 713 and the second text box 714. Accordingly, the user can easily grasp the relation between the detection result of the obtained neurite Nr and the first parameter.

The image overlapping button 721 is an input element configured to display an overlapping image between the captured image G1 and the detection result image G3 on the image display unit 800. When the image overlapping button 721 is clicked, the output controller 52 displays the overlapping image on the image display unit 800 of the result display screen 702. Accordingly, the user can compare the captured image G1 before the image processing and the detection result image G3 after the image processing, and can more accurately grasp the effect of the image processing method of the above-mentioned embodiment. When the image overlapping button 721 is clicked in a state in which the overlapping image is displayed on the image display unit 800, it is possible to make to a configuration in which either the captured image G1 or the detection result image G3 is displayed.

The re-execution button 722 is an input element configured to cause the data processing part 51 to execute processing from the first image processing to the binarization again and update the result display screen 702 so as to display a detection result of the neurite Nr obtained by the processing which was processed again on the display screen. When the re-execution button 722 is clicked, the output controller 52 displays the updated result display screen 702 on the output part 44. Here, the first image processing part 61 performs the first image processing using the first parameters input into the first text box 713 and the second text box 714.

The end button 723 is a button configured to terminate the processing using the image processing method of the variant by clicking the end button 723. When the end button 723 is clicked, the data processing part 51 terminates the processing as appropriate.

In the image processing method of the variant, since the user performs setting of the parameter in the image processing method while checking the captured image G1, the detection result image G3, and the like, as appropriate, it is possible to emphasize the linear portion accurately according to the aspect of the image.

(Variant 8)

In the above-mentioned Variant 7, when the numerical values input into the first text box 713 and the second text box 714 are not appropriate for the above-mentioned image processing, the notification can be displayed on the display screen.

Figure 22:
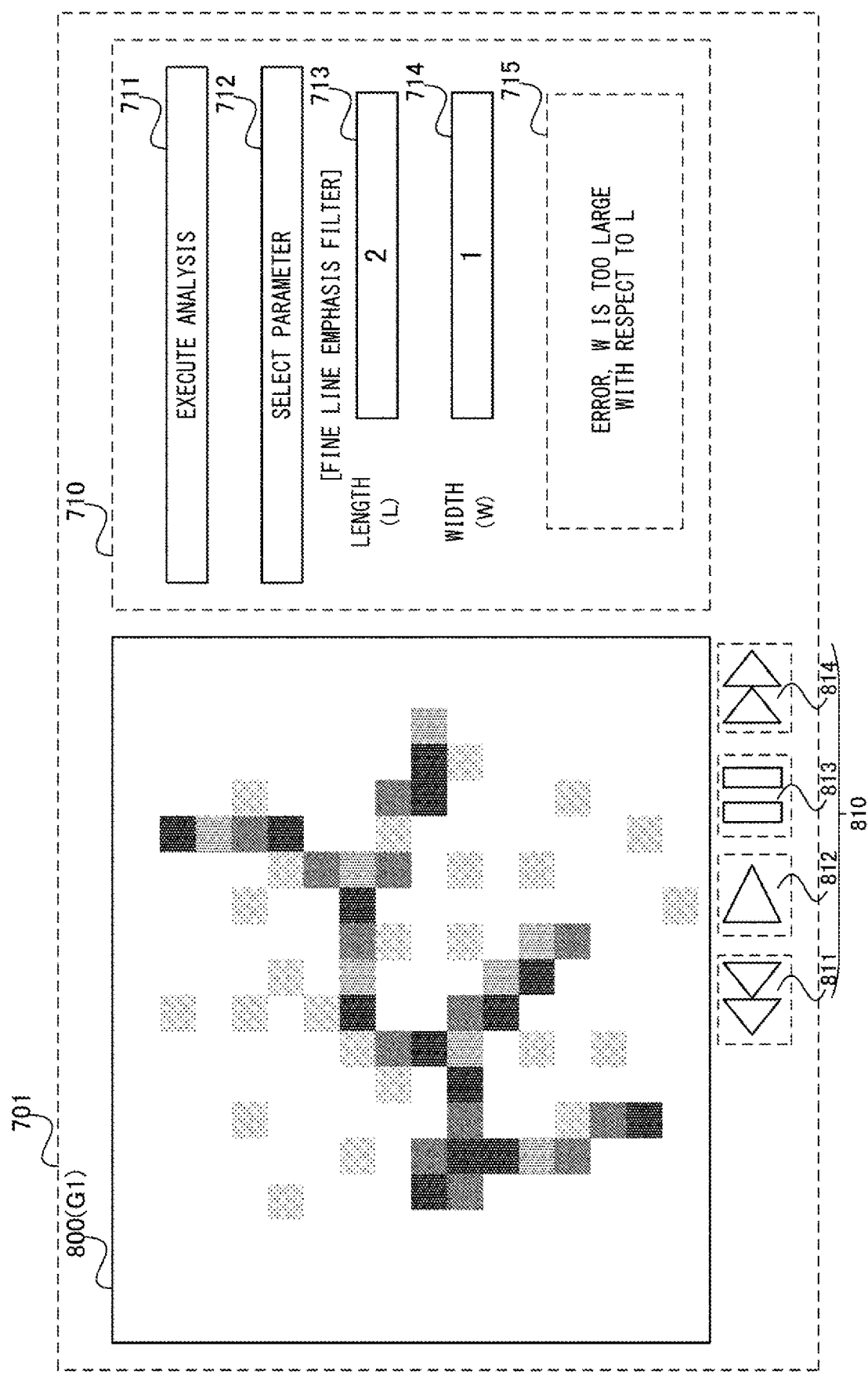
FIG. 22 is a conceptual view showing an example of a display screen according to Variant 8.

FIG. 22 is a conceptual view showing an aspect of a notification. The first input element display unit 715 of the basic screen 701 includes a notification display unit 715. The output controller 52 displays the notification on the notification display unit 715 when the numerical values input into the first text box 713 and the second text box 714 do not satisfy the predetermined condition. The predetermined condition may be, for example, a case in which lengths L of the one-dimensional filters F1, F11 and F12 are equal to or less than twice widths W of the one-dimensional filters F1, F11 and F12. In this case, as shown in FIG. 22, the output controller 52 can display the notification by characters such as "W is too large for L" on the notification display unit 715.

Further, the aspect of the notification is not particularly limited, and the output controller 52 may indicate the content of the notification by an image or the like instead of a character, or may give a voice warning or the like.

(Variant 9)

A program configured to realize an information processing function of the information processing part 40 of the above-mentioned embodiment may be recorded on a computer-readable recording medium, and a program recorded in the recording medium and related to the processing or the like by the data processing parts 51 and 51*a* such as the above-mentioned first image processing, second image processing, binarization, and the like, may be loaded into a computer system and executed. Further, "the computer system" disclosed herein includes an operating system (OS) or hardware such as peripheral devices. In addition, "the computer-readable recording medium" is referred to as a portable recording medium such as a flexible disk, a magneto-optical disk, an optical disk, a memory card, or the like, or a storage device such as a hard disk or the like installed in the computer system. Further, "the computer-readable recording medium" may include a medium that dynamically holds a program for a short time, such as a communication line when the program is transmitted via a network such as the Internet or the like or a communication circuit such as a telephone circuit or the like, or a medium that holds a program for a fixed time such as a volatile memory in a computer system that becomes a server or a client in this case. In addition, the program may be provided to realize a part of the above-mentioned function, and may be further realized by combining the above-mentioned function with the program already recorded in the computer system.

Figure 23:
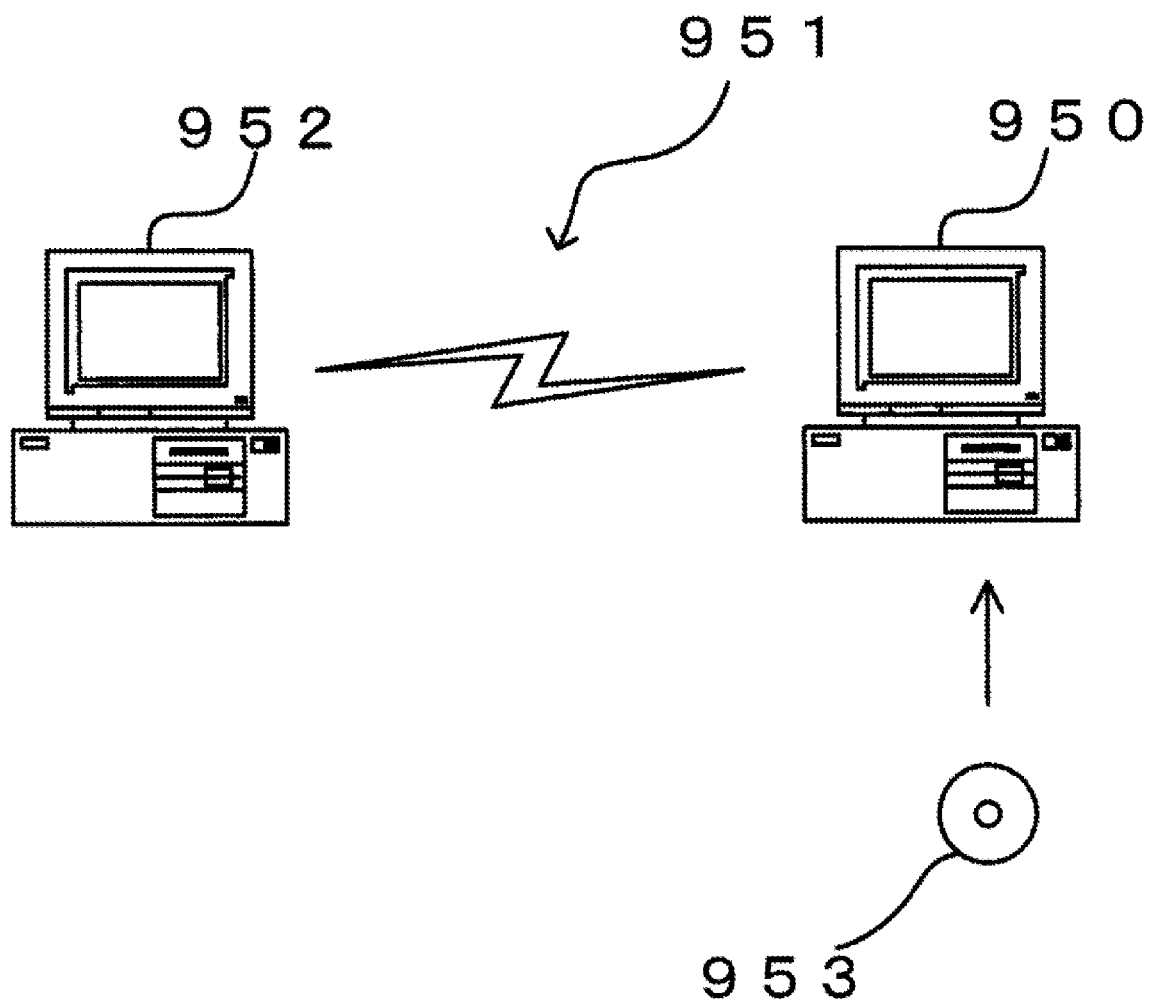
FIG. 23 is a conceptual view for describing provision of a program.

In addition, when the program is applied to a personal computer (hereinafter, referred to as PC) or the like, the program related to the above-mentioned control can be provided through a recording medium such as CD-ROM or the like, or data signal of the Internet or the like. FIG. 23 is a view showing the aspect. A PC 950 receives the program via a CD-ROM 953. In addition, the PC 950 has a connecting function to a communication circuit 951. A computer 952 is a server computer configured to provide the program, and stores the program in a recording medium such as a hard disk or the like. The communication circuit 951 is a communication circuit such as the Internet, a personal computer communication, or the like, a dedicated communication circuit, or the like. The computer 952 reads the program using the hard disk and transmits the program to the PC 950 via the communication circuit 951. That is, the program is carried as data signal by carrier waves and transmitted via the communication circuit 951. In this way, the program can be supplied as various types of computer-readable computer program products such as a recording medium, carrier waves, or the like.

As a program for realizing the above-mentioned information processing function, a program for causing the processing device (the controller 50) to perform the first image processing (corresponding to step S103 of the flowchart of FIG. 6) of setting the pixel values of the second pixel of the weighted image located at a position corresponding to the first pixel Px1 of the captured image G1 in the weighted image (second image) obtained by the image processing of the captured image (first image) G1 is included, the first image processing including first pixel group setting processing of setting the plurality of first pixel groups Pg1 set to correspond to the first pixel Px1 and disposed along in the plurality of directions that form the plurality of angles (the first angle 81) different from each other with respect to the predetermined direction (reference direction) in the captured image G1 or disposed along in the predetermined direction in each of the plurality of images obtained by moving the captured image G1 by the plurality of different angles (the first angle 81), first calculation processing (first pixel group setting processing and first calculation processing correspond to step S203 and S205) of calculating the plurality of first candidate pixel values on the basis of the sizes of the pixel values of the pixels in each of the plurality of first pixel groups Pg1, and first pixel value setting processing (corresponding to step S207) of setting the pixel values of the second pixels on the basis of the plurality of first candidate pixel values. Accordingly, it is possible to effectively emphasize the linear portion in the image.

In addition, when the variant is applied to an information processing system including a web server (hereinafter, also referred to as a server), a personal computer (hereinafter, referred to as a user terminal, or a PC), and the like, the information processing part 40 of the above-mentioned image processing device 1 is a web server including the communication part 42, the storage 43, the output part 44, and the data processing part 51. The information processing system outputs analysis results including the above-mentioned images (for example, a first image, a second image, a third image, and the like) to a user terminal through cloud computing via a network. For example, the information processing system includes a server, and the server includes a communication part (for example, the communication part 42) configured to acquire the first image or the like captured by the cultivation part 100, a storage (for example, the storage 43) configured to store the images (for example, a first image, a second image, a third image, and the like) or information required for the image analysis, a data processing part having the same function as the data processing part 51, and an output part (for example, the output part 44) configured to output analysis results of the images by the data processing part to a user terminal.

The present invention is not limited to the content of the embodiment. Other aspects that can be considered within the scope of the technical scope of the present invention are also included without departing from the scope of the present invention.

What is claimed is:

1. An image processing device comprising:
    a first image processing part configured to set a pixel value of a second pixel of a second image which is located at a position corresponding to a first pixel of a first image, which is obtained through imaging, in the second image obtained through image processing of the first image,
    a second image processing part configured to set a pixel value of a third pixel located at a position corresponding to the first pixel in a third image obtained by image processing of the first image, and a third image processing part configured to generate a weighted image on the basis of the pixel value of the second pixel processed by the first image processing part and the pixel value of the third pixel processed by the second image processing part, wherein the first image processing part comprises:

a first pixel group setting part configured to set a plurality of first pixel group which is set to correspond to the first pixel and which includes pixels disposed along in one direction;

a first calculation part configured to calculate a first candidate pixel values in each of the plurality of first pixel groups on the basis of a size of the pixel value of the pixel included in each of the plurality of first pixel groups; and a first pixel value setting part configured to set the pixel value of the second pixel of the second image on the basis of the plurality of first candidate pixel values, the second image processing part comprises:

a second pixel group setting part configured to set a plurality of second pixel groups which is set to correspond to the first pixel and which includes pixels disposed along in at least two directions;

a second calculation part configured to calculate a second candidate pixel value of each of a plurality of second pixel groups on the basis of a size of the pixel value of the pixel included in each of a plurality of second pixel groups; and a second pixel value setting part configured to set a pixel value of a third pixel of the third image on the basis of a plurality of second candidate pixel values.

2. The image processing device according to claim 1, wherein the first pixel group setting part is configured to set the plurality of first pixel groups which is disposed along a plurality of directions in each of the first image and which is a relationship in which a relative position between the first image and the first pixel group forms a plurality of angle different from each other, wherein the second pixel group setting part is configured to set the plurality of second pixel groups which is disposed along the at least two directions in each of the first image and which is a relationship in which a relative position between the first image and the second pixel group forms a plurality of angle different from each other, wherein the first calculation part calculates a plurality of first candidate pixel values on the basis of a sum or an average of a pixel value of a pixel included in each of a plurality of first pixel groups, and wherein the second calculation part calculates a plurality of second candidate pixel values on the basis of a sum or an average of a pixel value of a pixel included in each of a plurality of second pixel groups.

3. The image processing device according to claim 2, wherein the first image value setting part generates a first weighted image in which a linear portion in the second image is emphasized on the basis of the first candidate pixel, the second pixel value setting part generates a two-dimensional smoothing image in which a pixel value in the third image is not biased in a specific direction on the basis of the second candidate image, and the third image processing part generates a second weighted image in which the linear portion of the first weighted image is emphasized on the basis of a pixel value of the first weighted image and a pixel value of the two-dimensional smoothing image.

4. The image processing device according to claim 3, the third image processing part includes a binarization part configured to perform binarization of pixel values with respect to the second weighted image according to a plurality of different thresholds on the basis of a pixel value of a pixel included in each portion of the second weighted image.

5. The image processing device according to claim 1, wherein the first calculation part calculates the first candidate pixel value using a one-dimensional filter for the first pixel groups, and wherein the second calculation part calculates the second candidate pixel value using a two-dimensional filter for the first pixel groups.

6. The image processing device according to claim 1, wherein the first pixel value setting part sets a value of 0.8 times to 1.2 times the largest value or a value of 0.8 times to 1.2 times the smallest value among a plurality of first candidate pixel values as the pixel value of the second pixel.

7. The image processing device according to claim 1, wherein the first pixel group setting part sets a plurality of first pixel groups which is set to correspond to the first pixel and which is disposed along in a plurality of directions forming a plurality of angles different from each other with respect to a predetermined direction in the first image or which is disposed along in a predetermined direction in each of a plurality of image obtained by moving the first image at a plurality of angles different with each other with respect to a predetermined direction, and wherein the second pixel group setting part sets a plurality of second pixel groups which is disposed along in at least two directions obtained by rotating the at least two directions by a plurality of angles different from each other with respect to a predetermined direction in the first image or which is disposed along in the at least two directions in each of the first images rotated by a plurality of angles different with each other.

8. The image processing device according to claim 7, the third image processing part includes a first removing part configured to remove at least a part of a non-linear portion in the second image on the basis of the third image.

9. The image processing device according to claim 1, comprising:

a third pixel group setting part configured to set a plurality of third pixel groups which is set to correspond to the first pixel, which is disposed along in a plurality of directions that form a plurality of angles with respect to a predetermined direction of the first image or which is arranged in a predetermined direction in each of a plurality of images obtained by rotating the first image by a plurality of angles;

an information generating part configured to generate corresponding information of whether the first pixel corresponds to a linear portion in the first image on the basis of a sum or an average of pixel values of pixels included in a plurality of third pixel groups, and a processing controller configured to control processing of setting the first pixel group of the first pixel group setting part on the basis of the corresponding information generated by the information generating part.

10. The image processing device according to claim 9, wherein a number of the plurality of angles differs according to a position of the first pixel when the first pixel group setting part sets the plurality of first pixel groups, and
the processing controller sets the number at each position of the first image on the basis of the corresponding information.

11. The image processing device according to claim 10, wherein the processing controller determines whether the first pixel group setting part performs processing of setting the first pixel group at each position of the first image on the basis of the corresponding information.

12. The image processing device according to claim 9, comprising a second removing part configured to remove at least a part of a non-linear portion in the second image on the basis of the corresponding information generated by the information generating part.

13. The image processing device according to claim 1, comprising an input part configured to cause the first image processing part to input a position or a range of the first pixel that is an object of image processing.

14. The image processing device according to claim 1, wherein the first image is an image of a neurite or a blood vessel.

* * * * *